(12) United States Patent
Chun et al.

(10) Patent No.: US 11,066,704 B2
(45) Date of Patent: Jul. 20, 2021

(54) METHODS FOR PREPARING TAGGING OLIGONUCLEOTIDES

(71) Applicant: SEEGENE, INC., Seoul (KR)

(72) Inventors: Jong Yoon Chun, Seoul (KR); Gi-Seok Yoon, Seoul (KR)

(73) Assignee: SEEGENE, INC., Seoul (KR)

( * ) Notice: Subject to any disclaimer, the term of this patent is extended or adjusted under 35 U.S.C. 154(b) by 340 days.

(21) Appl. No.: 16/308,026

(22) PCT Filed: Jun. 9, 2017

(86) PCT No.: PCT/KR2017/006020
§ 371 (c)(1),
(2) Date: Dec. 7, 2018

(87) PCT Pub. No.: WO2017/213458
PCT Pub. Date: Dec. 14, 2017

(65) Prior Publication Data
US 2019/0309363 A1 Oct. 10, 2019

(30) Foreign Application Priority Data

Jun. 10, 2016 (KR) .................. 10-2016-0072263
Jun. 17, 2016 (KR) .................. 10-2016-0075518

(51) Int. Cl.
*C12Q 1/68* (2018.01)
*C12Q 1/6876* (2018.01)
*C12Q 1/6816* (2018.01)
*G16B 25/00* (2019.01)

(52) U.S. Cl.
CPC ............ *C12Q 1/6876* (2013.01); *C12Q 1/68* (2013.01); *C12Q 1/6816* (2013.01); *G16B 25/00* (2019.02); *C12Q 2525/161* (2013.01); *C12Q 2565/514* (2013.01)

(58) Field of Classification Search
CPC ............... C12Q 1/6876; C12Q 1/6818; C12Q 2525/161; C12Q 2565/514; C12Q 1/6811; C12Q 2563/179; G16B 25/00
See application file for complete search history.

(56) References Cited

U.S. PATENT DOCUMENTS

| | | | |
|---|---|---|---|
| 5,210,015 | A | 5/1993 | Gelfand et al. |
| 5,538,848 | A | 7/1996 | Livak et al. |
| 5,691,142 | A | 11/1997 | Dahlberg et al. |
| 6,194,149 | B1 | 2/2001 | Neri et al. |
| 6,358,691 | B1 | 3/2002 | Neri et al. |
| 2009/0227009 | A1 | 9/2009 | Sooknanan |
| 2012/0083418 | A1 | 4/2012 | Akitomi et al. |
| 2013/0210643 | A1 | 8/2013 | Casbon et al. |
| 2014/0080728 | A1* | 3/2014 | Nelson .................. C07H 21/00 506/9 |
| 2016/0140291 | A1 | 5/2016 | Zhang et al. |

FOREIGN PATENT DOCUMENTS

| | | |
|---|---|---|
| WO | 2012096523 A2 | 7/2012 |
| WO | 2012122571 A1 | 9/2012 |
| WO | 2012150835 A2 | 11/2012 |
| WO | 2013115442 A1 | 8/2013 |
| WO | 2014104818 A1 | 7/2014 |

OTHER PUBLICATIONS

Ye, J., et al., Primer-BLAST: A tool to design target-specific primers for polymerase chain reaction, BMC Bioinformatics, Jun. 18, 2012, vol. 13, No. 134, pp. 1-11.
European Search Report, dated Nov. 21, 2019, issued in corresponding application EP17810581.
Kaderali, L.; Primer Design for Multiplexed Genotyping; Methods in Molecular Biology, vol. 402; pp. 269-285, (2007).
Li, X., et al.; Universal Molecular Beacon-Based Tracer System for Real-Time Polymerase Chain Reaction; Anal. Chem. 2006, vol. 78, pp. 7886-7890.
Afonina, I., et al.; Primers with 5' flaps improve real-time PCR; BioTechniques, Dec. 2007, vol. 43; pp. 770-774.
Arora, N., et al.; Energetics of Base Pairs in B-DNA in Solution: An Appraisal of Potential Functions and Dielectric Treatments; J. Phys. Chem. B 1998, vol. 102, pp. 6139-6144.

* cited by examiner

*Primary Examiner* — David C Thomas
(74) *Attorney, Agent, or Firm* — Gianna Julian-Arnold; Saul Ewing Arnstein & Lehr LLP

(57) ABSTRACT

The present invention relates to technologies for preparing a tagging oligonucleotide. By analyzing exquisitely a non-complementarity level of a first tagging part, the first aspect of the present invention permits to more efficiently and easily select a suitable tagging sequence among a multitude of sequences generated theoretically. In addition, according to the second aspect of the present invention, when a nucleotide sequence for a tagging portion is first selected, one or more regions in a target nucleic acid sequence having a non-complementarity level to the nucleotide sequence for the tagging portion are found, and then a nucleotide sequence for a targeting portion is determined, tagging oligonucleotides for detecting various target nucleic acid sequences can prepared by using the fewest number of nucleotide sequences for the tagging portion and a third template.

18 Claims, 2 Drawing Sheets
Specification includes a Sequence Listing.

[Fig. 1]
100
110 — Selecting a hybridizable-complementary nucleotide sequence for a targeting portion and a non-hybridizable-non-complementary nucleotide sequence for a tagging portion in which a first tagging part is selected by an independent non-complementarity level
120 — Preparing a tagging oligonucleotide

[Fig. 2]
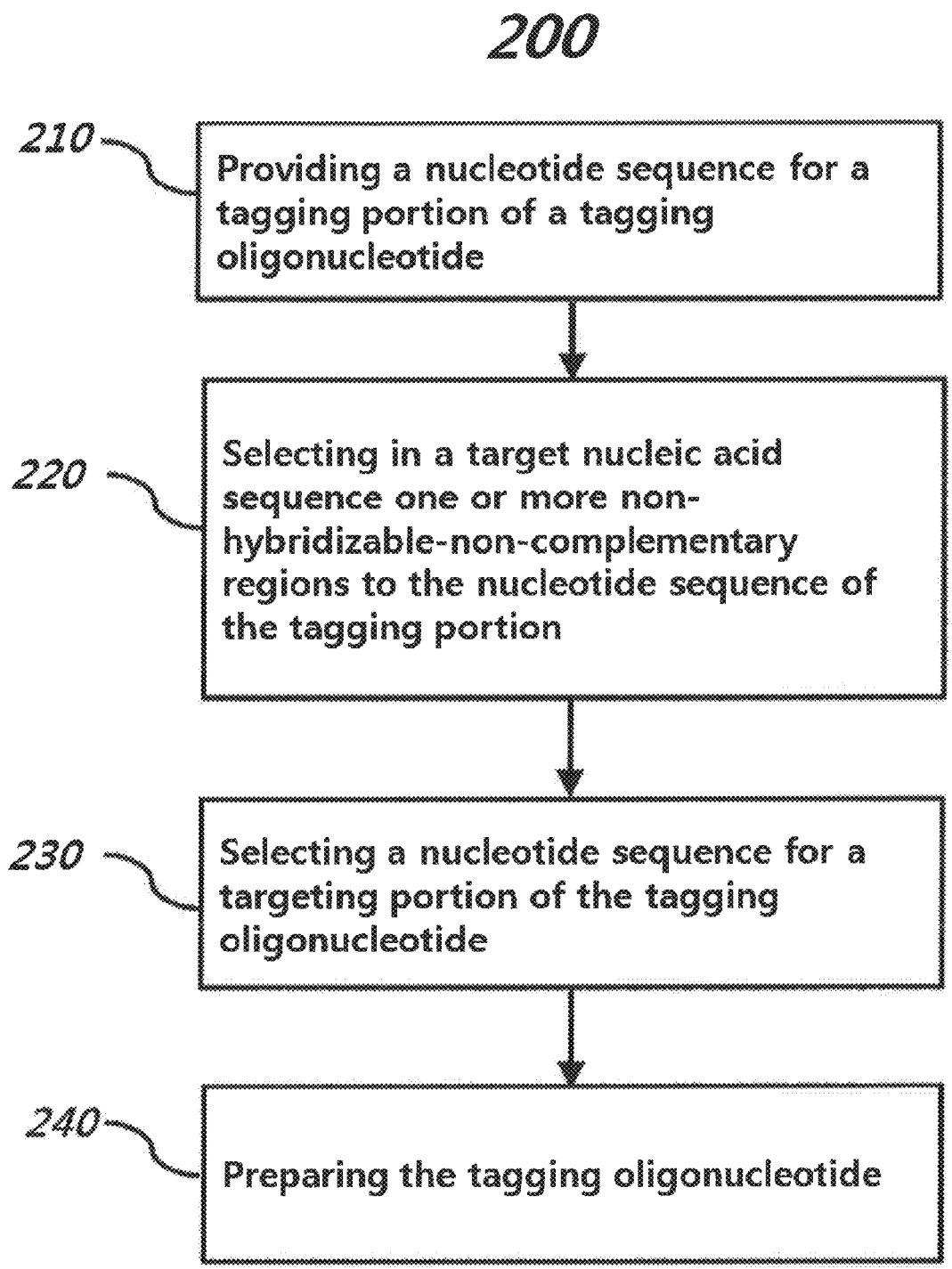

SEQUENCE LISTING

```
<160> NUMBER OF SEQ ID NOS: 43

<210> SEQ ID NO 1
<211> LENGTH: 19
<212> TYPE: DNA
<213> ORGANISM: Artificial Sequence
<220> FEATURE:
<223> OTHER INFORMATION: Synthetic nucleotide: Sequence of targeting
      portion for multiple F genes of human metapneumovirus

<400> SEQUENCE: 1
cctgcagatg ttggcatgt                                                 19

<210> SEQ ID NO 2
<211> LENGTH: 12
<212> TYPE: DNA
<213> ORGANISM: Artificial Sequence
<220> FEATURE:
<223> OTHER INFORMATION: Synthetic nucleotide: Sequence opposite to
      tagging portion

<400> SEQUENCE: 2
acagataaaa ct                                                        12

<210> SEQ ID NO 3
<211> LENGTH: 12
<212> TYPE: DNA
<213> ORGANISM: Artificial Sequence
<220> FEATURE:
<223> OTHER INFORMATION: Synthetic nucleotide: Sequence complementary to
      sequence of SEQ ID NO: 2

<400> SEQUENCE: 3
agttttatct gt                                                        12

<210> SEQ ID NO 4
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 4
acaaataaaa ct                                                        12

<210> SEQ ID NO 5
<211> LENGTH: 12
<212> TYPE: DNA
<213> ORGANISM: Artificial Sequence
<220> FEATURE:
```

<223> OTHER INFORMATION: Synthetic nucleotide:Sequence complementary to
      sequence of SEQ ID NO: 4

<400> SEQUENCE: 5
agttttattt gt                                                          12

<210> SEQ ID NO 6
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 6
gcagataaaa ct                                                          12

<210> SEQ ID NO 7
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 6

<400> SEQUENCE: 7
agttttatct gc                                                          12

<210> SEQ ID NO 8
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 8
acaaataaaa tt                                                          12

<210> SEQ ID NO 9
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 8

<400> SEQUENCE: 9
aattttattt gt                                                          12

<210> SEQ ID NO 10
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 10
acagataaaa tt                                                          12

<210> SEQ ID NO 11
<211> LENGTH: 12
<212> TYPE: DNA
<213> ORGANISM: Artificial Sequence
<220> FEATURE:
<223> OTHER INFORMATION: Synthetic nucleotide:Sequence complementary to sequence of SEQ ID NO: 10

<400> SEQUENCE: 11
aattttatct gt                                                           12

<210> SEQ ID NO 12
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 12
acagataaag ct                                                           12

<210> SEQ ID NO 13
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 12

<400> SEQUENCE: 13
agctttatct gt                                                           12

<210> SEQ ID NO 14
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 14
gcaaataaaa ct                                                           12

<210> SEQ ID NO 15
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 14

<400> SEQUENCE: 15
agttttattt gc                                                           12

<210> SEQ ID NO 16
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 16
gcagataaag ct                                                           12

<210> SEQ ID NO 17
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 16

```
<400> SEQUENCE: 17
agctttatct gc                                                         12

<210> SEQ ID NO 18
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 18
tcagataaaa ct                                                         12

<210> SEQ ID NO 19
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 18

<400> SEQUENCE: 19
agttttatct ga                                                         12

<210> SEQ ID NO 20
<211> LENGTH: 12
<212> TYPE: DNA
<213> ORGANISM: Artificial Sequence
<220> FEATURE:
<223> OTHER INFORMATION: Synthetic nucleotide:Sequence opposite to
      tagging portion

<400> SEQUENCE: 20
acaaataaac ct                                                         12

<210> SEQ ID NO 21
<211> LENGTH: 12
<212> TYPE: DNA
<213> ORGANISM: Artificial Sequence
<220> FEATURE:
<223> OTHER INFORMATION: Synthetic nucleotide:Sequence complementary to
      sequence of SEQ ID NO: 20

<400> SEQUENCE: 21
aggtttattt gt                                                         12

<210> SEQ ID NO 22
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 22
aagggacaga cg                                                         12

<210> SEQ ID NO 23
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 23
```

-continued

```
atagggcaga cg                                                       12

<210> SEQ ID NO 24
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 24
aaggagcaga cg                                                       12

<210> SEQ ID NO 25
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 25
aagaggcaga cg                                                       12

<210> SEQ ID NO 26
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 26
aacgggtaga cg                                                       12

<210> SEQ ID NO 27
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 27
aagggatgga cg                                                       12

<210> SEQ ID NO 28
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 28
atagggtgga cg                                                       12

<210> SEQ ID NO 29
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 29
aaagggcaga cg                                                       12

<210> SEQ ID NO 30
<211> LENGTH: 12
<212> TYPE: DNA
<213> ORGANISM: Artificial Sequence
```

```
<220> FEATURE:
<223> OTHER INFORMATION: Synthetic nucleotide:Tagging candidate sequence

<400> SEQUENCE: 30
aacggacaga cg                                                        12

<210> SEQ ID NO 31
<211> LENGTH: 12
<212> TYPE: DNA
<213> ORGANISM: Artificial Sequence
<220> FEATURE:
<223> OTHER INFORMATION: Synthetic nucleotide:Tagging candidate sequence

<400> SEQUENCE: 31
ataggacgga cg                                                        12

<210> SEQ ID NO 32
<211> LENGTH: 24
<212> TYPE: DNA
<213> ORGANISM: Artificial Sequence
<220> FEATURE:
<223> OTHER INFORMATION: Synthetic nucleotide:MP_F primer

<400> SEQUENCE: 32
cagctcaatc aggaatggtt tcac                                           24

<210> SEQ ID NO 33
<211> LENGTH: 24
<212> TYPE: DNA
<213> ORGANISM: Artificial Sequence
<220> FEATURE:
<223> OTHER INFORMATION: Synthetic nucleotide:MP_R primer

<400> SEQUENCE: 33
ctcagtttgc ccattgttta acca                                           24

<210> SEQ ID NO 34
<211> LENGTH: 12
<212> TYPE: DNA
<213> ORGANISM: Artificial Sequence
<220> FEATURE:
<223> OTHER INFORMATION: Synthetic nucleotide:Sequence of tagging
      portion (Tag-1)

<400> SEQUENCE: 34
gtcgtacgcg at                                                        12

<210> SEQ ID NO 35
<211> LENGTH: 12
<212> TYPE: DNA
<213> ORGANISM: Artificial Sequence
<220> FEATURE:
<223> OTHER INFORMATION: Synthetic nucleotide:Sequence of tagging
      portion (Tag-2)

<400> SEQUENCE: 35
cacgcgacga tt                                                        12

<210> SEQ ID NO 36
<211> LENGTH: 26
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 36
```

```
gaacaagcct tggacgctgg tacgca                                              26
```

<210> SEQ ID NO 37
<211> LENGTH: 27
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 37

```
gctcaccgtt cacgacacaa aggcacg                                             27
```

<210> SEQ ID NO 38
<211> LENGTH: 27
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 38

```
ggtacccgtg cctttgtgtc gtgaacg                                             27
```

<210> SEQ ID NO 39
<211> LENGTH: 27
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 39

```
gcttaagcac gccactaccc caagctt                                             27
```

<210> SEQ ID NO 40
<211> LENGTH: 27
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 40

```
gaacaagcct tggacgctgg tacgcaa                                             27
```

<210> SEQ ID NO 41
<211> LENGTH: 27
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 41

```
caaatcctgg tgggtgacaa acgcttg                                             27
```

<210> SEQ ID NO 42
<211> LENGTH: 28
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 42

```
caaatcctgg tgggtgacaa acgcttgt                                        28

<210> SEQ ID NO 43
<211> LENGTH: 28
<212> TYPE: DNA
<213> ORGANISM: Artificial Sequence
<220> FEATURE:
<223> OTHER INFORMATION: Synthetic nucleotide:Sequence of targeting
      portion

<400> SEQUENCE: 43
ccccaaagtg tgtcgactgc tagtgccg                                        28
```

METHODS FOR PREPARING TAGGING OLIGONUCLEOTIDES

TECHNICAL FIELD

This application claims priority from Korean Patent Application No. 2016-0072263, filed on Jun. 10, 2016 and Korean Patent Application No. 2016-0075518, filed on Jun. 17, 2016, in the Korean Intellectual Property Office, the disclosures of which are incorporated herein by reference.

The present invention relates to technologies for preparing a tagging oligonucleotide.

BACKGROUND ART

Hybridization between nucleic acids is a fundamental process in molecular biology and is affected by ionic strength, base composition, length of fragment to which the nucleic acid has been reduced, the degree of mismatching, and the presence of denaturing agents. Methods for amplifying a target nucleic acid sequence or detecting the presence of a target nucleic acid sequence using hybridization between an oligonucleotide such as a primer or a probe and a target nucleic acid sequence are widely used.

Polymerase chain reaction (hereinafter referred to as "PCR"), which is a representative nucleic acid amplification method, includes repeated cycles of denaturation of a double-stranded DNA, annealing of an oligonucleotide primer to a DNA template and primer extension by DNA polymerase. Most of primers used in the PCR method are composed of sequences that are hybridized with target nucleic acid sequences; however primers having a portion comprising a non-complementary sequence to a target nucleic acid sequence at the 5'-end are also used. Such non-complementary portion is used to provide a restriction site (Espelund, M. et al., 1992. BioTechniques 13:74-81), to provide a universal detection site (Li, X., et al., 2006. Anal. Chem. 78:7886-7890), or to increase amplification efficiency of PCR (Irina Afonina et al., 2007. BioTechniques 43:770-774).

A real-time detection method capable of detecting a target nucleic acid as monitoring the amplification degree of nucleic acids in a real time manner is widely used for detecting qualitatively or quantitatively a target nucleic acid. TaqMan method most extensively used generates a target signal by cleaving a double-labeled probe by 5'-nuclease activity of DNA polymerase (U.S. Pat. Nos. 5,210,015 and 5,538,848).

There have been known some methods using a probe comprising at its 5'-end a non-complementary portion to a target nucleic acid sequence. In Invader assay (U.S. Pat. Nos. 5,691,142, 6,358,691 and 6,194,149), such probe is cleaved by DNA polymerase or 5' FEN nuclease having 5' nuclease activity, a 5' flap portion having a non-complementary sequence to a target nucleic acid sequence is released, the 5' flap portion is then hybridized with a third oligonucleotide to form a cleavage structure, and a signal is finally generated by an additional cleavage reaction. Other methods using a probe having a portion comprising at the 5'-end or a 3'-end a non-complementary sequence to a target nucleic acid sequence are also known, including PTOCE (PTO cleavage and extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (WO 2014/104818) and POCH (PO Cleavage and Hybridization) method (WO2012-150835).

The non-complementary sequence portion to a target nucleic acid sequence is called as "a tagging portion", "a tag sequence", "a flap sequence", or "a tail sequence". Unlike a portion having a complementary sequence to the target nucleic acid sequence, the tagging portion in probes can be selected arbitrarily as long as it is non-complementary to the target nucleic acid sequence.

With the help of methods for preparing a tagging portion sequence suitable in a target amplification or detection, it will be possible to more efficiently and easily select a suitable tagging sequence among a multitude of sequences generated theoretically.

Meanwhile, when designing an oligonucleotide having the tagging portion, it is general that a sequence of a targeting portion is first determined and then a suitable sequence for the tagging portion is selected. In such a case, there are drawbacks in that methods using cleavage of tagging oligonucleotides require to design a new sequence of a tagging portion for each experiment in a dependent manner on a targeting portion and then to newly design an oligonucleotide to be hybridized with the tagging portion.

Throughout this application, various patents and publications are referenced and citations are provided in parentheses. The disclosure of these patents and publications in their entities are hereby incorporated by references into this application in order to more fully describe this invention and the state of the art to which this invention pertains.

DISCLOSURE OF INVENTION

Technical Problem

The present inventors have made intensive researches to develop a method for designing a tagging oligonucleotide or selecting a suitable tagging oligonucleotide from a tagging oligonucleotide dataset. As a result, we have found that when a first tagging part comprising a non-hybridizable-non-complementary nucleotide sequence to a target nucleic acid sequence adjacent to a targeting portion of the tagging oligonucleotide is selected by an independent non-complementarity level in preparation of the tagging oligonucleotide, the tagging oligonucleotide serving as a primer or a probe (particularly, a probe) can be prepared in a more efficient manner.

Furthermore, for methods of detecting a target nucleic acid sequence by using a tagging oligonucleotide and a third template which hybridizes with a tagging portion of the tagging oligonucleotide, the present inventors have made intensive researches to develop a method for detecting various target nucleic acid sequences using nucleotide sequences as few as possible for the tagging portion and nucleotide sequences as few as possible for the third template. As a result, we have found that when the nucleotide sequence for the tagging portion is first selected, one or more regions in the target nucleic acid sequence having a non-complementarity level to the nucleotide sequence for the tagging portion are found, and then a nucleotide sequence for a targeting portion is determined, tagging oligonucleotides for detecting various target nucleic acid sequences can prepared by using the fewest number of nucleotide sequences for the tagging portion and the third template.

Accordingly, it is an object of this invention to provide a method for preparing a tagging oligonucleotide.

It is another object of this invention to provide a computer readable storage medium containing instructions to configure a processor to perform a method for preparing a tagging oligonucleotide.

Other objects and advantages of the present invention will become apparent from the detailed description to follow taken in conjugation with the appended claims and drawings.

Solution to Problem

I. First Aspect of a Method of Preparing a Tagging Oligonucleotide

In one aspect of the present invention, there is provided a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, comprising:

(a) selecting the hybridizable-complementary nucleotide sequence to the target nucleic acid sequence for the targeting portion and the non-hybridizable-non-complementary nucleotide sequence to the target nucleic acid sequence for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the target nucleic acid sequence; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and (b) preparing the tagging oligonucleotide comprising (i) the targeting portion comprising the selected hybridizable-complementary nucleotide sequence and (ii) the tagging portion comprising the selected non-hybridizable-non-complementary nucleotide sequence.

The present inventors have made intensive researches to develop a method for designing a tagging oligonucleotide or selecting a suitable tagging oligonucleotide from a tagging oligonucleotide dataset. As a result, we have found that when a first tagging part comprising a non-hybridizable-non-complementary nucleotide sequence to a target nucleic acid sequence adjacent to a targeting portion of the tagging oligonucleotide is selected by an independent non-complementarity level in preparation of the tagging oligonucleotide, the tagging oligonucleotide serving as a primer or a probe (particularly, a probe) can be prepared in a more efficient manner.

The term used herein "tagging oligonucleotide" refers to an oligonucleotide, which comprises a targeting portion comprising a hybridizable-complementary nucleotide sequence to a target nucleic acid sequence and a tagging portion comprising a non-hybridizable-non-complementary nucleotide sequence to the target nucleic acid sequence. Particularly, the tagging oligonucleotide refers to an oligonucleotide comprising a portion that is hybridized with the target nucleic acid sequence to form a double strand and a portion that is not hybridized with the target nucleic acid sequence to have a single strand. More particularly, the targeting portion of the tagging oligonucleotide is a portion comprising a complementary nucleotide sequence to be hybridized with the target nucleic acid sequence, and the tagging portion is a portion comprising a non-complementary nucleotide sequence not to be hybridized with the target nucleic acid sequence under a stringent condition.

The tagging oligonucleotide is useful as a probe and a primer, and may be used for a variety of assays.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. For maximum efficiency of amplification, particularly the primer is a single stranded. Particularly, the primer is deoxyribonucleotide. The primers used in this invention may be comprised of naturally occurring dNMP (i.e., dAMP, dGM, dCMP and dTMP), modified nucleotide, or non-natural nucleotide. The primers may also include ribonucleotides.

The primer must be sufficiently long to prime the synthesis of extension products in the presence of the agent for polymerization. The exact length of the primers will depend on many factors, including temperature, application, and source of primer.

The term used herein "probe" refers to a single-stranded nucleic acid molecule comprising a portion or portions that are substantially complementary to a target nucleic acid sequence. The probe may include a label capable of generating a signal for target detection.

The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof. The term used "hybridizing" used herein refers to the formation of a double-stranded nucleic acid from complementary single stranded nucleic acids. There is no intended distinction between the terms "annealing" and "hybridizing", and these terms will be used interchangeably.

The tagging oligonucleotide includes two types of oligonucleotides: (i) a 5'-tagging oligonucleotide comprising in a 5' to 3' direction the tagging portion and the targeting portion; and (ii) a 3'-tagging oligonucleotide comprising in a 3' to 5' direction the tagging portion and the targeting portion. Particularly, the tagging oligonucleotide prepared by the present invention is the 5'-tagging oligonucleotide.

The term "oligonucleotide" as used herein refers to a linear oligomer of natural or modified monomers or linkages, including deoxyribonucleotides and ribonucleotides, capable of specifically hybridizing with a target nucleotide sequence, whether occurring naturally or produced synthetically. The oligonucleotide is particularly single stranded for maximum efficiency in hybridization. Particularly, the oligonucleotide is an oligodeoxyribonucleotide. The oligonucleotide of this invention can be comprised of naturally occurring dNMP (i.e., dAMP, dGM, dCMP and dTMP), nucleotide analogs, or nucleotide derivatives. The oligonucleotide can also include ribonucleotides.

The oligonucleotide may include nucleotides with backbone modifications such as peptide nucleic acid (PNA) (M. Egholm et al., Nature, 365:566-568 (1993)), locked nucleic acid (LNA) (WO1999/014226), bridged nucleic acid (BNA) (WO2005/021570), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The term used herein "target nucleic acid sequence" refers to a nucleic acid sequence of interest for amplification or detection using the tagging oligonucleotide of the present invention, and may be abbreviated herein as "target" or "target sequence". The target nucleic acid sequence may be in a double strand or single strand. Where the target nucleic acid sequence is in a double strand, each strand may be named as a forward strand or a reverse strand. It may be also named as a (+) strand (coding strand, sense strand, non-template strand) or a (−) strand (noncoding strand, antisense strand, template strand).

The first aspect of the present invention will be described with reference to FIG. 1 as follows:

Step (a): Selection of the Targeting Portion and the Tagging Portion (110)

According to the present invention, the present invention comprises selecting the hybridizable-complementary nucleotide sequence to the target nucleic acid sequence for the targeting portion and the non-hybridizable-non-complementary nucleotide sequence to the target nucleic acid sequence for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the target nucleic acid sequence; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part.

The tagging oligonucleotide prepared by the present invention comprises the targeting portion and the tagging portion.

The term used herein "targeting portion" refers to a portion that hybridizes with the target nucleic acid sequence to form a double strand.

The term used herein "tagging portion" refers to a portion that does not hybridize with the target nucleic acid sequence to form a single strand.

The targeting portion comprises a hybridizable-complementary nucleotide sequence to a target nucleic acid sequence. The term "hybridizable-complementary nucleotide sequence" used herein to describe the targeting portion comprises not only a sequence that is perfectly complementary to a target nucleic acid sequence, but also a sequence that is sufficient to specifically hybridize to a target nucleic acid sequence under certain stringent conditions. For example, the term "hybridizable-complementary nucleotide sequence" may comprise one or more non-complementary nucleotides (i.e., mismatch). For example, it may comprise 1-2, 1-3, 1-4, or 1-6 non-complementary nucleotides. The term "hybridizable-complementary nucleotide sequence" has a different meaning from the term "perfectly complementary". In particular, the targeting portion comprises a nucleotide sequence that is perfectly complementary to the target nucleic acid sequence.

The length of the targeting portion is not particularly limited and may be, for example, 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides, or 20-30 nucleotides.

The tagging portion comprises a non-hybridizable-non-complementary nucleotide sequence to a target nucleic acid sequence. The term "non-hybridizable-non-complementary nucleotide sequence" used herein to describe a tagging portion comprises not only a sequence that is perfectly non-complementary to a target nucleic acid sequence but also a sequence that is sufficient to not hybridize to a target nucleic acid sequence under certain stringent conditions. For example, the term "non-hybridizable-non-complementary nucleotide sequence" may comprise one or more complementary nucleotides (i.e., match). For example, it may comprise 1-2, 1-3, 1-4, or 1-6 complementary nucleotides. The term "non-hybridizable-non-complementary nucleotide sequence" has a different meaning from the term "perfectly non-complementary".

The length of the tagging portion is not particularly limited and may be, for example, 7-48 nucleotides, 7-40 nucleotides, 7-30 nucleotides, 7-20 nucleotides, 10-48 nucleotides, 10-40 nucleotides, 10-30 nucleotides, 10-20 nucleotides, 12-48 nucleotides, 12-40 nucleotides, 12-30 nucleotides, or 12-20 nucleotides.

The tagging portion comprises the first tagging part adjacent to the targeting portion and the second tagging part adjacent to the first tagging part.

In hybridization of the tagging oligonucleotide with the target nucleic acid sequence, the first tagging part is the most critical part to cause a single strand of the tagging portion.

The length of the first tagging part may be, for example, 2-8 nucleotides, 2-7 nucleotides, 2-6 nucleotides, 2-5 nucleotides, 2-4 nucleotides, 2-8 nucleotides, 2-7 nucleotides, 2-6 nucleotides, 2-5 nucleotides, 3-8 nucleotides, 3-7 nucleotides, 3-6 nucleotides, 3-5 nucleotides, 3-4 nucleotides, 4-8 nucleotides, 4-7 nucleotides, 4-6 nucleotides, or 4-5 nucleotides.

The first tagging part may occupy 20-40%, 20-35%, 20-30%, 25-40%, 25-35%, 25-30%, 30-40%, or 30-35% of the entire sequence of the tagging portion.

The length of the second tagging part may be, for example, 4-40 nucleotides, 4-30 nucleotides, 4-25 nucleotides, 4-20 nucleotides, 4-15 nucleotides, 4-12 nucleotides, 4-10 nucleotides, 4-6 nucleotides, 6-40 nucleotides, 6-30 nucleotides, 6-25 nucleotides, 6-20 nucleotides, 6-15 nucleotides, 6-12 nucleotides, 6-10 nucleotides, 8-40 nucleotides, 8-30 nucleotides, 8-25 nucleotides, 8-20 nucleotides, 8-15 nucleotides, 8-12 nucleotides, or 8-10 nucleotides.

In one embodiment of the present invention, the first tagging part may comprise 30% or less, 25% or less, 20% or less, or 15% or less complementary nucleotides to the opposite nucleotide sequence on a target nucleic acid sequence to the extent that the first tagging part does not hybridize with the opposite nucleotide sequence.

In one embodiment of the present invention, the second tagging part may comprise 80% or less, 70% or less, 60% or less, 50% or less, 40% or less, 30% or less, or 20% or less complementary nucleotides to the opposite nucleotide sequence on a target nucleic acid sequence to the extent that the second tagging part does not hybridize with the opposite nucleotide sequence.

In the Specification, a sequence opposite to the tagging portion or the first tagging part refers to a sequence on a target nucleic acid sequence that is present oppositely to the tagging portion or the first tagging part, when the tagging oligonucleotide in 5' to 3' direction is hybridized with the target nucleic acid sequence in 3' to 5' direction.

According to an embodiment of this invention, the non-hybridizable-non-complementary nucleotide sequence in the tagging portion, the hybridizable-complementary nucleotide sequence in the targeting portion, or the non-hybridizable-non-complementary nucleotide sequence in the tagging portion and the hybridizable-complementary nucleotide sequence in the targeting portion is selected or provided from a pre-established dataset of tagging portion candidates or a pre-established dataset of targeting portion candidates.

For example, when designing the tagging portion to include n nucleotides, there may be a dataset that includes $4^n$ tagging portion candidates. The tagging portion selected or provided may be obtained by sorting in suitable candidates and/or sorting out unsuitable candidates among candidates of the dataset.

The tagging portion is selected or provided from the dataset of candidates, and the targeting portion may be obtained by manually selecting a complementary sequence in consideration of the target nucleic acid sequence. Alternatively, a non-complementary sequence to the target nucleic acid sequence is manually selected as the tagging portion, and the targeting portion may be obtained by selecting from the dataset of candidates. Alternatively, both the tagging portion and the targeting portion may be obtained by selecting or providing from the dataset of candidates.

According to an embodiment of this invention, the non-hybridizable-non-complementary nucleotide sequence in the tagging portion, the hybridizable-complementary nucleotide sequence in the targeting portion, or the non-hybridizable-non-complementary nucleotide sequence in the tagging portion and the hybridizable-complementary nucleotide sequence in the targeting portion is selected or provided in consideration of the nucleotide sequence of the target nucleic acid sequence.

For example, both the tagging portion and the targeting portion may be manually selected or provided in consideration of the target nucleic acid sequence. Alternatively, the tagging portion is selected or provided from the dataset of candidates, and the targeting portion may be obtained by manually selecting a complementary sequence in consideration of the target nucleic acid sequence. Alternatively, a non-complementary sequence to the target nucleic acid sequence is manually selected or provided as the tagging portion and the targeting portion may be obtained by selecting from the dataset of candidates.

According to an embodiment of the present invention, the nucleotide sequence for the tagging portion is selected as a universal tagging portion with a range of application coverage.

According to an embodiment, the range of application coverage may include coverages for all organisms, organisms belonging to one kingdom, phylum, class, order, family, genus or species, eukaryotic cells, prokaryotic cells, bacteria, virus, fungi, a certain classification stage of viruses according to the International Committee on Taxonomy of Viruses (ICTV) classification (e.g., virus of certain species, or virus of certain subfamily), a certain classification stage of viruses according to the Baltimore classification (e.g., virus of certain species, or virus of certain subfamily), or all or some of diversity sequences of a gene exhibiting genetic diversity.

According to one embodiment of the present invention, the sequence provided as the nucleotide sequence for the tagging portion comprises a sequence known as tagging portions in the art. For example, the nucleotide sequence for the tagging portion may be selected from nucleotide sequences suitable for tagging portions being publicly accessible.

According to an embodiment, the nucleotide sequence for the tagging portion is a sequence stored in and retrievable from a database.

According to conventional methods for preparing tagging oligonucleotides, the tagging portion is designed such that its entire sequence is non-complementary to the target nucleic acid sequence by taking into account the entire sequence rather than a partial sequence. Under prior arts, one of skill in the art for designing a sequence of the tagging portion would not require or address designing of a partial sequence of the tagging portion in a separated or independent manner. According to the present invention, the sequence selection is performed by an independent non-complementarity level for the partial sequence of the tagging portion, i.e., the first tagging part. This technical feature as the most prominent feature of the present invention is firstly proposed by the present inventors.

The present inventors have found that such technical feature allows for preparing more efficiently and surely tagging oligonucleotides with excellent functions as probes that are specifically hybridized with a target nucleic acid sequence and then endonucleolytically cleaved.

The non-hybridizable-non-complementary nucleotide sequence of the first tagging part is selected by an independent non-complementarity level such that a sequence with a non-complementarity level satisfying a predetermined threshold value criterion may be selected as the non-hybridizable-non-complementary nucleotide sequence.

The term used herein "selected by an independent non-complementarity level" with referring to the first tagging part means that a non-complementarity level of the first tagging part is determined (e.g., calculated) separately from a sequence of the other part and then a sequence of the first tagging part is selected in consideration of the determined non-complementarity level. For preparing the tagging oligonucleotide, it is necessary to analyze and determine whether a sequence to be selected is a hybridizable nucleotide sequence complementary to a target nucleic acid sequence (used as the targeting portion) or a non-hybridizable nucleotide sequence non-complementary to a target nucleic acid sequence (used as the tagging portion). Accordingly, the term "selected by an independent non-complementarity level" does not exclude analysis of complementarity or non-complementarity to the target nucleic acid sequence for other sequences as well as the first tagging part.

The term used herein "non-complementarity level" refers to the degree to which the tagging portion or a part of the tagging portion (e.g., the first tagging part) does not form Watson-Crick base pairs with a target nucleic acid sequence. The term "non-complementarity level" may be used interchangeably with the ordinary term "non-complementarity" in the art, but particularly the term "non-complementarity level" means a value representing binding unfavorability between nucleotide bases.

For example, although the base pairs (AG), (AC) and (AA) are all expressed as non-complementary base pairs, their unfavorabilities based on the binding force are different from each other. The term "non-complementarity level" may be expressed particularly by using the unfavorability based on such binding force.

The unfavorability may be provided based on the binding force between the nucleotide bases, and be quantified for each base pair considering the binding force. The binding force between two nucleotide bases is affected by the type of base pairs, a surrounding sequence and the like.

The results of the binding force calculation (e.g., bond energy) may be interpreted as 'favorability' and also as 'unfavorability'. Unless otherwise indicated, the binding force calculation result is interpreted as 'unfavorability' and analysis examples based on unfavorability are described hereinbelow. In the present Specification, the descriptions based on unfavorability may be applied to methods using favorability. Such drafting strategy is intended to concisely and clearly explain the present invention without undue redundancy.

According to the present invention, a score may be given in consideration of the binding force for each base pair and used as the unfavorability.

Alternatively, a ranking may be given in consideration of the binding force for each base pair, a score may be then given for each ranking or ranking section, and the score may be used as the unfavorability. The non-complementarity level between sequences comprising a plurality of nucleotides may be obtained from the unfavorability of each base pair.

The higher the non-complementarity level of a sequence is, the more suitable it is as the sequence of the first tagging part. The non-complementarity level may be quantified (e.g., numericized) using a variety of methods. Particularly, the non-complementarity level used in the present invention is a quantified or numericized non-complementarity level.

The selection of the nucleotide sequence of the first tagging part is carried out by selecting a sequence of which non-complementarity level satisfies a predetermined threshold value criterion. The threshold value may be determined empirically or theoretically. According to an embodiment, the non-complementarity level used in the selection of the nucleotide sequence of the first tagging part may be obtained or evaluated by the unfavorability between the nucleotide bases. According to an embodiment, when the binding force between a base pair is lower, a higher score is given and the score is used as unfavorability; and when the non-complementarity level is calculated using the unfavorability, the selection of the nucleotide sequence of the first tagging part is performed by selecting a sequence having a non-complementarity level that is equal to or larger than the predetermined threshold value.

Alternatively, when the binding force is lower, a lower score is given and the score may be used as the unfavorability. When the non-complementarity level is calculated using the unfavorability to which the score is given in this way, the selection of the nucleotide sequence of the first tagging part is performed by selecting a sequence having a non-complementarity level that is smaller than or equal to the predetermined threshold value.

As the alternative example, 'when the binding force is lower, a lower score is given, and the score may be used as the unfavorability' may be expressed as 'when the binding force is lower, a lower score is given, and the score may be used as the favorability'. The non-complementarity level may be calculated using the favorability to which the score is given in this way. In this case, the selection of the nucleotide sequence of the first tagging part is performed by selecting a sequence having a non-complementarity level that is smaller than or equal to the predetermined threshold value.

Alternatively, 'when the binding force is lower, a higher score is given, and the score may be used as the unfavorability' may be expressed as 'when the binding force is lower, a higher score is given, and the score may be used as the favorability'. The non-complementarity level may be calculated using the favorability to which the score is given in this way. In this case, the selection of the nucleotide sequence of the first tagging part is performed by selecting a sequence having a non-complementarity level that is equal to or larger than the predetermined threshold value.

The binding force calculation results may be interpreted as 'unfavorability' and 'favorability'. Unless otherwise indicated, the binding force calculation results are interpreted as 'unfavorability' and the present invention is described using the term 'unfavorability' in order to concisely and clearly explain the present invention without undue redundancy.

When nucleotide bases are paired, their binding force (or bond energy) may be calculated using a variety of methods known in the art. For example, the bond energy value between the nucleotide bases may be obtained by MM2, MM3, MM4, OPLS, OPLS-AA, AMBER, GROMOS, CHARMM, Xplor, Discover, MMFF and Tripos method or force field method, and the unfavorability or favorability value based on the bond energy value may be obtained (see: Reviews in Computational Chemistry, Vol 16, Lipkowitz and Boyd, eds., John Wiley & Sons, New York, N.Y. (2000); Nidhi Arora et al., J. Phys. Chem. B, 102:6139(1998)).

According to an embodiment, the score may be given under assumption that a base pair between the same bases has the lowest binding force, a base pair between complementary bases has the highest binding force and the other combinations have an intermediate binding force.

The value of the binding force (e.g., bond energy) per se that is calculated by the methods described above may be adopted as the unfavorability or favorability.

Alternatively, the score is given for each base pair in consideration of the bond energy value calculated by the methods described above, and the score may be used for calculating the unfavorability or favorability. For example, assuming that the bond energy values between base pairs is (AA)=(TT)=(GG)=(CC)<(TC)=(AG)=(AC)=(TG)<(AT)=(GC), the unfavorability may be given as 1.3 points for (AA), (TT), (GG) and (CC) base pairs, 1.0 point for (TC), (AG), (AC) and (TG) base pairs and 0 point for (AT) and (GC) base pairs. Using the score, the unfavorability of the first tagging part to the target nucleic acid sequence may be calculated and the non-complementarity level may be calculated based on the unfavorability.

According to an embodiment, the unfavorability may be given as 0 point for (AA), (TT), (GG) and (CC) base pairs, 1.0 point for (TC), (AG), (AC) and (TG) base pairs and 1.3 points for (AT) and (GC) base pairs. Alternatively, the favorability may be given as 0 point for (AA), (TT), (GG) and (CC) base pairs, 1.0 point for (TC), (AG), (AC) and (TG) base pairs and 1.3 points for (AT) and (GC) base pairs. According to another embodiment, the favorability may be given as 1.3 points for (AA), (TT), (GG) and (CC) base pairs, 1.0 point for (TC), (AG), (AC) and (TG) base pairs and 0 point for (AT) and (GC) base pairs.

According to an embodiment of the present invention, the non-complementarity level may be provided by scores given depending on unfavorability of the bonds between nucleotide bases A, T, G and C. The non-complementarity level calculated using the scores is named as "a first tagging part score". Particularly, the non-complementarity level is the sum or the product of the scores given depending on unfavorability of the bonds between nucleotide bases A, T, G and C.

More particularly, the non-complementarity level for the first tagging part may be obtained by summing the scores given to the base pairs between the first tagging part and a nucleotide sequence located oppositely to the first tagging part.

For example, where the sequence of the first tagging part is 5'-AGTC-3' and the sequence of the target nucleic acid located oppositely to the first tagging part is 3'-GGTA-5', the unfavorability of the first tagging part calculated by the first approach becomes 1.0+1.3+1.3+1.0=4.6. When the predetermined threshold value is 3.0, the 4.6 point is more than the threshold value and therefore 5'-AGTC-3' may be selected as the sequence of the first tagging part.

There are a variety of ways to give the scores to bonds between nucleotide base pairs.

According to an embodiment, the scores given depending on unfavorability of the bonds between the nucleotide bases are assigned such that the sum of scores given for a first tagging part of which all nucleotides are not involved in Watson-Crick base pairing is greater than the sum of scores given for a first tagging part of which one or two nucleotides are involved in Watson-Crick base pairing.

According to an embodiment, the non-hybridizable-non-complementary nucleotide sequence of the tagging portion is selected from sequences that satisfy one or more of the following criteria (particularly, two or more of criteria, more particularly, four or more of criteria, still more particularly, six or more of criteria, still much more particularly, eight or more of criteria, most particularly, nine of criteria):

(i) exclusion of a mononucleotide run sequence, $(A)_n$, $(T)_n$, $(G)_n$ or $(C)_n$, in which n is at least 4;

(ii) inclusion of a sequence with 30-80% (particularly, 40-80%, 40-70%, 50-70%, 55-70%, for example, 50%, 55%, 60%, 65% and 70%) GC content;

(iii) exclusion of a sequence of the tagging portion immediately adjacent to the targeting portion in which G and/or C is consecutively located in the number of 8 or more (particularly, 7 or more, 6 or more, 5 or more, 4 or more or 3 or more);

(iv) when the tagging portion forms a homodimer, exclusion of a sequence in which the ratio of nucleotides involved in the formation of the homodimer (for example, nucleotides forming A/T and G/C base pairs in homodimer) is 70% or more (particularly, 60% or more, more particularly, 65% or more) based on a total nucleotide number of the tagging portion;

(v) when the tagging portion forms a homodimer, exclusion of a sequence in which the ratio of consecutive nucleotides involved in the formation of the homodimer is 65% or more (particularly, 50% or more, more particularly, 55% or more) based on a total nucleotide number of the tagging portion;

(vi) when the tagging portion forms the tagging oligonucleotide together with the targeting portion, exclusion of a sequence rendering ΔG value for a hairpin structure of the tagging oligonucleotide to become −8.0 kcal/mol or less (particularly, −5.0 kcal/mol or less, more particularly, −4.0 kcal/mol or less, more particularly, −3.0 kcal/mol or less, more particularly, −2.5 kcal/mol or less, more particularly, −2.0 kcal/mol or less, more particularly, −1.5 kcal/mol or less, more particularly, −1.0 kcal/mol or less);

(vii) when there is a complementary nucleotide in the first tagging part, exclusion of a sequence in which the complementary nucleotide is located at a position of 0-1 nucleotide apart from a nucleotide of the first tagging part immediately adjacent to the targeting portion;

(viii) inclusion of a sequence in which a nucleotide of the first tagging part immediately adjacent to the targeting portion is A or T;

(ix) when the tagging portion forms a heterodimer with a primer for amplification of the target nucleic acid sequence, exclusion of a sequence in which the ratio of nucleotides involved in the formation of the heterodimer (for example, nucleotides forming A/T and G/C base pairs in heterodimer) is 40% or more (particularly, 30% or more, or 20% or more) based on a total nucleotide number of the tagging portion;

(x) when the tagging portion forms a heterodimer with a primer for amplification of the target nucleic acid sequence, exclusion of a sequence in which the ratio of consecutive nucleotides involved in the formation of the heterodimer is 40% or more (particularly, 30% or more, 20% or more, or 15% or more) based on a total nucleotide number of the tagging portion;

(xi) when the tagging oligonucleotide forms a heterodimer with another oligonucleotide, exclusion of a sequence in which the ratio of nucleotides involved in the formation of the heterodimer is 70% or more (65% or more, 60% or more, 55% or more, 50% or more, or 40% or more) based on a total nucleotide number of the tagging oligonucleotide; and (xii) when the tagging oligonucleotide forms a heterodimer with another oligonucleotide, exclusion of a sequence in which the ratio of consecutive nucleotides involved in the formation of the heterodimer is 60% or more (55% or more, 50% or more, or 40% or more) based on a total nucleotide number of the tagging oligonucleotide.

The advantages of the present invention become more apparent for detecting a plurality of target nucleic acid sequences when a single tagging oligonucleotide may be commonly applied to detection of the plurality of target nucleic acid sequences According to an embodiment, the target nucleic acid sequence comprises a plurality of target nucleic acid sequences, the tagging oligonucleotide (particularly, one tagging oligonucleotide) is used for detection of all of the plurality of target nucleic acid sequences, and the plurality of target nucleic acid sequences comprise (i) sequences located oppositely to the targeting portion of the tagging oligonucleotide are identical to each other and (ii) sequences located oppositely to the tagging portion are identical to or different from each other (more particularly, different from each other).

The sequences of the target nucleic acid sequence located on opposite to the tagging portion may have 1-8, 1-7, 1-6, 1-4 or 1-3 different nucleotides from each other.

According to an embodiment, the target nucleic acid sequence comprises a plurality of nucleic acid sequences for a sequence exhibiting genetic diversity, the tagging oligonucleotide is used for detection of all of the plurality of target nucleic acid sequences, and the non-hybridizable-non-complementary nucleotide sequence of the first tagging part or the tagging portion is selected such that its non-complementarity levels to all of the plurality of target nucleic acid sequences satisfy a predetermined threshold value criterion.

According to an embodiment, the tagging portion is located on opposed to a variation site of the sequence exhibiting genetic diversity, and the targeting portion is hybridized with a conserved region in the sequence exhibiting genetic diversity.

The genetic diversity has been reported in various genomes. The genetic diversity is most frequently found and occurs in viral genomes (Nathalie B. et al., Journal of Clinical Microbiology, 42:3532(2004); Tersa C. et al., Journal of Infectious Diseases, 185:1660(2002); Takashi E. et al., Journal of Clinical Microbiology, 42:126(2004); and Elizabeth R. et al. Clinical Infectious Diseases, 32:1227(2001)). According to an embodiment, the target nucleic acid sequence is a plurality of nucleic acid sequences for one gene of a virus having genetic diversity.

According to one embodiment of the present invention, the target nucleic acid sequence comprises nucleic acid sequences of subclass organisms belonging to a higher class organism (for example, where the target nucleic acid sequence is the VP1 gene of norovirus, the target nucleic acid sequence may comprise VP1-encoding nucleic acid sequences of the subclass (genotypes 1 and 2) belonging to norovirus)

The present invention is very useful for preparing a tagging oligonucleotide that may be used to detect the target nucleic acid sequence exhibiting genetic diversity by using a single tagging oligonucleotide.

According to an embodiment of the present invention, the non-hybridizable-non-complementary nucleotide sequence of the first tagging part or the tagging portion is selected such that the mean value of its non-complementarity levels to the plurality of target nucleic acid sequences satisfy the predetermined threshold value criterion.

The mean value of its non-complementarity levels of the first tagging part and the tagging portion is named as "first tagging part score average" and "tagging portion score average", respectively.

For example, the non-complementarity level is evaluated by comparing the sequence of the first tagging part to a plurality of target nucleic acid sequences (A1, A2 and A3) (for example, calculation of the unfavorability using scores given to base pairs). Where the non-complementarity levels were 4.9, 4.0 and 4.3 for A1, A2 and A3, respectively (the average value 4.4) and the threshold value is 4.0, the sequence of the first tagging part is then selected because the first tagging part score average is more than the threshold value.

According to an embodiment of the present invention, the non-hybridizable-non-complementary nucleotide sequence of the first tagging part or the tagging portion is selected such that among all of the plurality of target nucleic acid sequences a proportion of nucleic acid sequences to which the non-complementarity levels of the first tagging part or the tagging portion satisfy a predetermined threshold value criterion is equal to or greater than a predetermined proportion criterion. The proportion is named as "pass ratio".

In the above example, since the non-complementarity levels of the sequence of the first tagging part to all of three target nucleic acid sequences are more than the threshold value, the pass ratio is 100%. If a predetermined proportion criterion of the pass ratio is 90%, the sequence of the first tagging part is selected to be used for the tagging oligonucleotide.

Particularly, the pass ratio is 80% or more, more particularly 85% or more, still more particularly 90% or more, still further more particularly 95% or more, most particularly 100% or more.

More particularly, the non-hybridizable-non-complementary nucleotide sequence of the first tagging part or the tagging portion is selected only when the first tagging part score average (or the tagging portion score average) and the pass ratio are both more than a predetermined threshold value. For example, in the above example, since the first tagging part score average and the pass ratio are both more than the threshold value, the sequence of the first tagging part is selected to be used for the tagging oligonucleotide. Assumed that the non-complementarity levels of the first tagging part are 4.9, 3.6 and 4.0 for A1, A2 and A3, respectively (the average value 4.17), the pass ratio becomes 75% being less than a predetermined proportion criterion and therefore the sequence of the first tagging part is evaluated to be unsuitable for the tagging oligonucleotide.

According to an embodiment of the present invention, the non-hybridizable-non-complementary nucleotide sequence of the tagging portion is selected such that a non-complementarity level of an entire sequence of the tagging portion satisfies a predetermined threshold value criterion.

For example, the non-complementarity level of the entire sequence of the tagging portion is selected to be more than a predetermined threshold value, the non-complementarity level of the sequence of the first tagging part in the selected sequence is then evaluated in an independent manner, and the selected sequence is finally determined as the tagging portion for the tagging oligonucleotide when the non-complementarity level of the sequence of the first tagging part is more than a predetermined threshold value.

According to another embodiment of the present invention, the selection of the non-complementary nucleotide sequence to the target nucleic acid sequence for the tagging portion is performed by selecting the nucleotide sequence of the first tagging part and then (i) selecting the nucleotide sequence of the second tagging part such that the non-complementarity level of the entire sequence of the tagging portion satisfies the predetermined threshold value criterion or (ii) selecting the nucleotide sequence of the second tagging part such that the non-complementarity level of the entire sequence of the tagging portion has the largest value.

According to an embodiment, the non-complementarity level of the entire sequence of the tagging portion is obtained by unfavorability between nucleotide bases. According to an embodiment, the unfavorability is a weighted unfavorability in which weighting values are assigned to the tagging portion in a successively increasing manner from a location of the second tagging part most distant from the targeting portion to a location of the first tagging part most adjacent to the targeting portion.

For example, when the tagging portion is composed of 12 nucleotides, the weighting values of "1, 4, 9, 16, 25, 36, 49, 64, 81, 100, 121 and 144" or "2, 3, 4, 6, 9, 12, 14, 21, 28, 30, 45 and 60" are given from a location of the second tagging part most distant from the targeting portion to a location of the first tagging part most adjacent to the targeting portion, the unfavorability of the entire sequence of the tagging portion may be calculated using the weighting values and the scores as unfavorability of base pairs (e.g., multiply the weighting values by the unfavorability score), thereby obtaining the non-complementarity level.

The non-complementarity level in the method of the present invention may be ranked and sequences may be selected according to the ranking For example, as the first tagging part, a plurality of sequences with non-complementarity levels satisfying a predetermined threshold value criterion may be ranked according to their non-complementarity levels. For example, as the tagging portion, a plurality of sequences with non-complementarity levels satisfying a predetermined threshold value criterion may be ranked according to their non-complementarity levels.

As described above, the ranking of the sequences may be determined by various criteria for their entire sequences or partial sequences. The ranking methods may be combined to provide sequences in a new rank.

By applying additional sequence selection criteria, sequences with priority or optimal sequences may be more effectively selected.

According to one embodiment, the nucleotide sequence of the targeting portion is selected from sequences that satisfy one or more of the following criteria:

(i) inclusion of a sequence with 30-80% GC content (particularly, 40-70% or 40-65%);

(ii) inclusion of a sequence having a $T_m$ value of 35° C. to 85° C. (particularly, 50° C. to 85° C. or 55° C. to 80° C.);

(iii) when the tagging oligonucleotide is a probe used with a primer for amplifying the target nucleic acid sequence, inclusion of a sequence having a $T_m$ value being 3° C. to 25° C. (particularly, 5° C. to 20° C., 5° C. to 15° C. or 10° C. to 15° C.) higher than a $T_m$ value of the primer; and (iv) when the tagging oligonucleotide is used in a cleavage reaction by 5' nuclease activity, inclusion of a sequence of which 5'-end or 5'-penultimate nucleotide is G or C.

Where there are candidate nucleotide sequences for a plurality of the targeting portions, the selection criteria may be further applied to select more suitable nucleotide sequences for the targeting portion. Furthermore, when a selection criterion capable of ranking is applied, a ranked nucleotide sequences for the targeting portions may be provided.

According to an embodiment, the hybridizable-complementary nucleotide sequence of the targeting portion is first selected and then as the tagging portion selected is the non-hybridizable-non-complementary nucleotide sequence to a sequence of the target nucleic acid sequence adjacent to a sequence with which the targeting portion is hybridized.

According to an embodiment of the present invention, the non-hybridizable-non-complementary nucleotide sequence of the tagging portion is first selected and then as the targeting portion selected is the hybridizable-complementary nucleotide sequence to a sequence of the target nucleic acid sequence adjacent to a sequence opposite to the sequence of the tagging portion.

Step (b): Preparation of the Tagging Oligonucleotide (120)

Afterwards, the tagging oligonucleotide comprising (i) the targeting portion comprising the selected hybridizable-complementary nucleotide sequence and (ii) the tagging portion comprising the selected non-hybridizable-non-complementary nucleotide sequence is prepared.

The term used herein "preparing or preparation" with referring to the tagging oligonucleotide comprises provision of an oligonucleotide sequence and manufacture of an oligonucleotide molecule.

In the method of the present invention, one or more nucleotide sequences may be provided as the nucleotide sequence for the tagging portion, and one or more nucleotide sequences for the targeting portion for each tagging portion provided may be selected.

Where the plurality of tagging oligonucleotides is prepared, a selection criteria may be further applied to select more suitable tagging oligonucleotides. Furthermore, when a selection criterion capable of ranking is applied, the tagging oligonucleotides ranked may be prepared.

According to an embodiment, the tagging oligonucleotide prepared is selected from oligonucleotides that satisfy one or more of the following criteria:

(i) exclusion of a tagging oligonucleotide in which ΔG value for a hairpin structure is −8.0 kcal/mol or less (particularly, −5.0 kcal/mol or less, −4.0 kcal/mol or less, −3.0 kcal/mol or less, −2.5 kcal/mol or less, −2 kcal/mol or less, −1.5 kcal/mol or less, −1.0 kcal/mol or less);

(ii) when the tagging oligonucleotide forms a homodimer, exclusion of a tagging oligonucleotide in which the ratio of nucleotides involved in the formation of the homodimer is 70% or more (particularly, 65% or more, more particularly, 60% or more);

(iii) when the tagging oligonucleotide forms a homodimer, exclusion of a tagging oligonucleotide in which the ratio of consecutive nucleotides involved in the formation of the homodimer is 65% or more (particularly, 60% or more, more particularly, 55% or more);

(iv) when the tagging oligonucleotide forms a heterodimer with another oligonucleotide, exclusion of a tagging oligonucleotide in which the ratio of nucleotides involved in the formation of the heterodimer is 70% or more (particularly, 65% or more, more particularly, 60% or more); and (v) when the tagging oligonucleotide forms a heterodimer with another oligonucleotide, exclusion of a tagging oligonucleotide in which the ratio of consecutive nucleotides involved in the formation of the heterodimer is 65% or more (particularly, 60% or more, more particularly, 55% or more).

According to an embodiment of the present invention, the tagging oligonucleotide prepared by the present invention is used as a primer or a probe.

According to an embodiment, the tagging oligonucleotide prepared by the present invention is a probe to be used with a primer pair to amplify the target nucleic acid sequence hybridized with the tagging oligonucleotide. In this case, it is necessary to evaluate the probe together with the primer pair in view of target detection or amplification (for example, analysis of formation of a heterodimer).

According to an embodiment, the tagging oligonucleotide prepared by the present invention is a plurality of probes to be used with a primer pair to amplify the target nucleic acid sequence hybridized with the tagging oligonucleotide. In this case, it is necessary to evaluate with other oligonucleotides that coexist (for example, analysis of the formation of heterodimers)

In a tagging primer prepared by the present invention, the tagging portion may be used to confer a restriction enzyme site or a universal detection site, or to increase amplification efficiency of PCR.

A tagging probe prepared by the present invention may be used for a variety of methods involving the cleavage step of the tagging portion such as INVADER assay (U.S. Pat. Nos. 5,691,142, 6,358,691 and 6,194,149), PTOCE method (WO 2012/096523), PCE-SH method (WO 2013/115442), PCE-NH method (WO 2014/104818) and POCH method (WO 2012/150835).

Storage Medium, Device and Program

In another aspect of this invention, there is provided a computer readable storage medium containing instructions to configure a processor to perform a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, the method comprising:

(a) selecting the hybridizable-complementary nucleotide sequence to the target nucleic acid sequence for the targeting portion and the non-hybridizable-non-complementary nucleotide sequence to the target nucleic acid sequence for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the target nucleic acid sequence; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and (b) preparing the tagging oligonucleotide comprising (i) the targeting portion comprising the selected hybridizable-complementary nucleotide sequence and (ii) the tagging portion comprising the selected non-hybridizable-non-complementary nucleotide sequence.

In still another aspect of this invention, there is provided a computer program to be stored on a computer readable storage medium, to configure a processor to perform a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, the method comprising:

(a) selecting the hybridizable-complementary nucleotide sequence to the target nucleic acid sequence for the targeting portion and the non-hybridizable-non-complementary nucleotide sequence to the target nucleic acid sequence for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the target nucleic acid sequence; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and (b) preparing the tagging oligonucleotide comprising (i) the targeting portion comprising the selected hybridizable-complementary nucleotide sequence and (ii) the tagging portion comprising the selected non-hybridizable-non-complementary nucleotide sequence.

In another aspect of this invention, there is provided a device for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, comprising (a) a computer processor, and (b) a computer readable storage medium of the present method coupled to the computer processor.

Since the storage medium, the device and the computer program of the prevent invention are intended to perform the present methods described hereinabove in a computer, the common descriptions between them are omitted in order to avoid undue redundancy leading to the complexity of this specification.

The program instructions are operative, when performed by the processor, to cause the processor to perform the present method described above. The program instructions for performing the method of preparing the tagging oligonucleotide may comprise the following instructions: (i) an instruction to select the hybridizable-complementary nucleotide sequence to the target nucleic acid sequence as the targeting portion and the non-hybridizable-non-complementary nucleotide sequence to the target nucleic acid sequence as the tagging portion; and (ii) an instruction to prepare the tagging oligonucleotide (e.g., displaying on output device) comprising the targeting portion and the tagging portion comprising the selected nucleotide sequences.

The present method is implemented in a processor, such as a processor in a stand-alone computer, a network attached computer or a data acquisition device.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The tagging oligonucleotide may be provided in a variety of ways. For example, the sequence of the tagging oligonucleotide may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the sequence of the tagging oligonucleotide may be provided to a server system via a network connection (e.g., LAN, VPN, Internet, intranet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

The computer processor may be prepared in such a manner that a single processor can do several performances. Alternatively, the processor unit may be prepared in such a manner that several processors do the several performances, respectively.

II. Second Aspect of a Method of Preparing a Tagging Oligonucleotide

In another aspect of the present invention, there is provided a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, comprising:

(a) providing a nucleotide sequence for the tagging portion; wherein the tagging portion comprises a first tagging part adjacent to the targeting portion and a second tagging part adjacent to the first tagging part;

(b) selecting in the target nucleic acid sequence one or more non-hybridizable-non-complementary regions to the nucleotide sequence for the tagging portion by (i) selecting at least one region in the target nucleic acid sequence and (ii)

evaluating a non-complementarity level of the selected at least one region to the nucleotide sequence for the tagging portion;

(c) selecting a nucleotide sequence for the targeting portion by (i) selecting a nucleotide sequence with a predetermined length in the target nucleic acid sequence that is adjacent to the non-hybridizable-non-complementary region to the nucleotide sequence of the tagging portion and (ii) selecting a hybridizable-complementary nucleotide sequence to the selected nucleotide sequence in the target nucleic acid as the nucleotide sequence for the targeting portion; and (d) preparing the tagging oligonucleotide comprising the nucleotide sequence of the tagging portion provided in the step (a) and the nucleotide sequence of the targeting portion selected in the step (c).

For methods of detecting a target nucleic acid sequence using a tagging oligonucleotide and an artificial template which hybridizes with a tagging portion of the tagging oligonucleotide, the present inventors have made intensive researches to develop a method for detecting various target nucleic acid sequences using nucleotide sequences as few as possible for a tagging portion and nucleotide sequences as few as possible for the artificial template. As a result, we have found that when the nucleotide sequence for the tagging portion is first selected, one or more regions in the target nucleic acid sequence having a non-complementarity level to the nucleotide sequence for the tagging portion are found and then a nucleotide sequence for the targeting portion is determined, tagging oligonucleotides for detecting various target nucleic acid sequences can prepared by using the fewest number of nucleotide sequence for the tagging portion and the artificial template.

Conventional methods for detecting target nucleic acid sequences using the tagging oligonucleotide and the third template which hybridizes with its tagging portion generally first select a nucleotide sequence of the targeting portion to be hybridized with the target nucleic acid sequence, and then a nucleotide sequence of the tagging portion is selected in considering a nucleotide sequence located on opposite to the tagging portion. Because the sequence of the tagging portion is designed differently depending on hybridization positions of the targeting portion with reference to the target nucleic acid sequence and therefore the third template to be hybridized with the tagging portion has to be newly designed, the conventional methods are cost-ineffective and time-ineffective.

The inventors of the present invention have found that the problem of the conventional methods can be solved by firstly selecting the nucleotide sequence for the tagging portion and then selecting the nucleotide sequence of the targeting portion.

It is noteworthy that the present method permits to efficiently detect various nucleic acid sequences even using a single type of the third template with a certain nucleotide sequence. Conventional real-time PCR methods using different labeled probes depending on nucleic acid sequences to be detected have shortcomings in the senses that different labeled probes are synthesized with significant costs and amounts usually larger than required for target detection. Therefore, after experiments, it is often to discard remaining labeled-probes. Where the tagging oligonucleotide is prepared according to the method of the present invention, the detection of various nucleic acid sequences by a real-time detection method becomes true using a single type of the third template.

Since the terms of "tagging oligonucleotide", "primer", "probe", "annealing", "priming", "oligonucleotide" and "target nucleic acid sequence" can be described with reference to descriptions in the first aspect of the present invention, the common descriptions between them are omitted in order to avoid undue redundancy leading to the complexity of this specification.

The second aspect of the method of the present invention will be described with reference to FIG. 2 as follows:

Step (a): Provision of a Nucleotide Sequence for the Tagging Portion (210)

A nucleotide sequence for the tagging portion is firstly provided. The tagging portion comprises a first tagging part adjacent to the targeting portion and a second tagging part adjacent to the first tagging part.

Unlike conventional methods of firstly determining the nucleotide sequence of the targeting portion and then selecting the nucleotide sequence of the tagging portion, the method of the present invention firstly provides a certain nucleotide sequence as the tagging portion.

Although an arbitrarily selected sequence may be provided as the nucleotide sequence of the tagging portion, it is particular that the nucleotide sequence provided is an empirically or theoretically selected sequence found to be suitable for the tagging portion.

According to an embodiment of the present invention, the nucleotide sequence for the tagging portion is designed such that the sequence is solely not hybridized with the target nucleic acid sequence under given stringent conditions.

Since the descriptions for "the tagging portion or the targeting portion which is selected or provided from a pre-established dataset of tagging portion candidates or a pre-established dataset of targeting portion candidates", "the tagging portion or the targeting portion which is selected or provided in consideration of the target nucleic acid sequence", "a range of application coverage", and "the tagging portion and selection thereof" in the second aspect of the present invention are the same as those of the first aspect of the present invention, the common descriptions between them are omitted in order to avoid undue redundancy leading to the complexity of this specification.

According to an embodiment of the present invention, the nucleotide sequence for the tagging portion in the step (a) comprises at least two nucleotide sequences, the selected nucleotide sequence for the targeting portion in the step (c) comprises at least two nucleotide sequences, and said preparing the tagging oligonucleotide in the step (d) is performed by preparing each of at least two tagging oligonucleotides using one of the at least two nucleotide sequences for the tagging portion and a corresponding nucleotide sequence of the targeting portion among the at least two nucleotide sequences of the targeting portion.

The tagging oligonucleotide prepared by the present invention comprises the targeting portion and the tagging portion.

Since the descriptions for the terms "targeting portion", "tagging portion", "hybridizable-complementary nucleotide sequence", "non-hybridizable-non-complementary nucleotide sequence", "the length of the targeting portion" and "the length of the tagging portion" in the second aspect of the present invention are the same as those of the first aspect of the present invention, the common descriptions between them are omitted in order to avoid undue redundancy leading to the complexity of this specification.

The tagging portion comprises the first tagging part adjacent to the targeting portion and the second tagging part adjacent to the first tagging part.

The first tagging part means a part of the tagging portion that is relatively closer to the targeting portion among parts of the tagging portion. The second tagging part means a part of the tagging portion that is relatively apart from the targeting portion among parts of the tagging portion. Particularly, when the tagging oligonucleotide is hybridized with the target nucleic acid sequence, the first tagging part becomes the most critical part in forming a single strand without hybridization of the tagging portion with the target nucleic acid sequence. Particularly, the second tagging part is a part that may require a non-complementarity level lower than that of the first tagging part to the target nucleic acid sequence. Sequences may be selected so as not to achieve stable hybridization of only the second tagging part under reaction conditions.

In this specification, the tagging portion is described to comprise two separate parts, the first tagging part and the second tagging part. However, such descriptions are not intended to restrict selection of a non-hybridizable-non-complementary region in step (b) to selection in separately considering each of the first tagging part and the second tagging part. That is, it is clear to those skilled in the art reading this specification that the selection in step (b) is carried out in consideration of an entire tagging portion and/or at least one of the two parts.

Since the descriptions for "the length or ratio of the first tagging part or the second tagging part" and "a sequence opposite to the tagging portion or the first tagging part" in the second aspect of the present invention are the same as those of the first aspect of the present invention, the common descriptions between them are omitted in order to avoid undue redundancy leading to the complexity of this specification.

According to an embodiment of this invention, when two or more nucleotide sequences for the tagging portion are provided, the nucleotide sequences for the tagging portion are selected such that the nucleotide sequences of the first tagging part among the tagging portions are more diverse.

Step (b): Selection of One or More Non-Hybridizable-Non-Complementary Regions to the Nucleotide Sequence for the Tagging Portion (220)

Afterwards, one or more non-hybridizable-non-complementary regions to the nucleotide sequence for the tagging portion are selected in the target nucleic acid sequence by (i) selecting at least one region in the target nucleic acid sequence and (ii) evaluating a non-complementarity level of the selected at least one region to the nucleotide sequence for the tagging portion.

According to an embodiment of this invention, after evaluating a non-complementarity level of the selected at least one region of the of the step (b), the present invention further comprises (iii) selecting the selected at least one region as the non-hybridizable-non-complementary region of the target nucleic acid sequence when the non-complementarity level of the selected at least one region satisfies a criterion. Particularly, the criterion is a predetermined threshold value criterion.

In the present invention, the one or more regions in the target nucleic acid sequence is selected such that it is a non-hybridizable-non-complementary region to the nucleotide sequence for the tagging portion.

According to one embodiment, the non-hybridizable-non-complementary regions to the nucleotide sequence for the tagging portion are selected in a certain region of the target nucleic acid sequence. For example, when the tagging oligonucleotide is a probe and the target nucleic acid sequence is a sequence to be amplified, the non-hybridizable-non-complementary region is selected in an amplified region of the target nucleic acid sequence. Where the tagging oligonucleotide is a primer, the non-hybridizable-non-complementary region is selected in a region on which the primer is to be located.

One or more regions in the target nucleic acid sequence may be present. The regions in the target nucleic acid sequence are present in the nucleic acid sequence strand with which the tagging oligonucleotide hybridizes.

The expression used herein "evaluating a non-complementarity level of the selected at least one region to the nucleotide sequence for the tagging portion" means evaluating a non-complementarity level to an entire sequence or a partial sequence (e.g., the first tagging part) for the tagging portion.

According to an embodiment of this invention, the at least one region selected in the target nucleic acid sequence is a region having a length corresponding to the nucleotide sequence for the tagging portion. According to an embodiment, the evaluation of the non-complementarity level of the selected at least one region in the target nucleic acid sequence in the step (b) is performed by evaluating the non-complementarity level to an entire sequence of the nucleotide sequence for the tagging portion. The evaluation is performed to analyze whether the non-complementarity level of the selected at least one region in the target nucleic acid sequence to an entire sequence for the tagging portion satisfies a predetermined threshold value criterion.

According to an embodiment of the present invention, the at least one region selected in the target nucleic acid sequence is a region having a length corresponding to the nucleotide sequence for the first tagging part among the tagging portion. According to an embodiment, the evaluation of the non-complementarity level of the selected at least one region in the target nucleic acid sequence in the step (b) is performed by evaluating the non-complementarity level to the first tagging part of the nucleotide sequence for the tagging portion in an independent manner. The evaluation is performed to analyze whether the non-complementarity level of the selected at least one region in the target nucleic acid sequence to the first tagging part satisfies a predetermined threshold value criterion.

The first tagging part is a part which plays the most critical role in forming a single strand without hybridization of the tagging portion with the target nucleic acid sequence. Therefore, evaluating the non-complementarity level of the selected at least one region in the target nucleic acid sequence to the nucleotide sequence for the first tagging part helps to more efficiently find candidate regions with higher non-hybridization-non-complementarity.

According to an embodiment, the evaluation of a non-complementarity level of the selected at least one region to the nucleotide sequence for the tagging portion is performed by evaluating both the non-complementarity level to the entire nucleotide sequence of the tagging portion and an independent non-complementarity level to the nucleotide sequence for the first tagging part.

According to an embodiment, the selection of the selected at least one region as the non-hybridizable-non-complementary region of the target nucleic acid sequence is performed by selecting sequence regions that satisfy both the criterion (particularly, the predetermined threshold value criterion) for the non-complementarity level to the entire nucleotide sequence of the tagging portion and a criterion (particularly, a predetermined threshold value criterion) for an independent non-complementarity level to the nucleotide sequence for the first tagging part.

The regions in the target nucleic acid sequence that satisfy a criterion for the non-complementarity level to the entire nucleotide sequence of the tagging portion is firstly found and then analyzed whether the regions in the target nucleic acid sequence satisfies a criterion for the non-complementarity level to the first tagging part. Alternatively, the regions in the target nucleic acid sequence that satisfy a criterion for the non-complementarity level to the nucleotide sequence for the first tagging part is firstly found and then analyzed whether regions in the target nucleic acid sequence specified by the regions found with regard to the first tagging part satisfy a criterion of the non-complementarity level to the entire nucleotide sequence of the tagging portion.

The non-complementarity level required for the tagging portion and the non-complementarity level required for the first tagging part may be different from or identical to each other. The criterion (particularly, the predetermined threshold value criterion) for the non-complementarity level of the entire tagging region may be different from or identical to that for the independent non-complementarity level of the first tagging part.

A plurality of non-hybridizable-non-complementary regions may be searched in the target nucleic acid sequence for a sequence of the tagging portion. According to one embodiment of the present invention, the regions in the target nucleic acid sequence that satisfy the criterion (particularly, the predetermined threshold value criterion) for the non-complementarity level are ranked depending on the non-complementarity level. According to one embodiment, the regions in the target nucleic acid sequence are ranked by the non-complementarity level to the entire tagging portion, the non-complementarity level to the first tagging part, the non-complementarity level to the second tagging part, or a combination thereof. According to an embodiment, the criterion (particular, the predetermined threshold value criterion) may be lowered such that more candidate regions may be selected.

The term used herein "non-complementarity level" in conjunction with the region of the target nucleic acid sequence refers to the degree to which the region does not form Watson-Crick base pairs with the tagging portion or a part of the tagging portion (e.g., the first tagging part). The term "non-complementarity level" may be used interchangeably with the ordinary term "non-complementarity" in the art, but particularly the term "non-complementarity level" means a value representing binding unfavorability between nucleotide bases.

The term "non-complementary level" may be expressed as the number of nucleotides that does not form Watson-Crick base pairs, the number of nucleotides that form Watson-Crick base pairs, or a combination thereof, or a ratio of the above-indicated number to a total length of a sequence (e.g., the entire tagging portion or the first tagging part).

According to an embodiment of the present invention, the non-complementarity level to the first tagging part or the second tagging part is obtained by using the number of nucleotides involved in Watson-Crick base pairs.

According to an embodiment, the non-complementarity level to the first tagging part may comprise positions of nucleotides involved in Watson-Crick base pairs. In this case, the criterion may be allowability or scores for positions of nucleotides involved in Watson-Crick base pairs.

According to an embodiment, the one or more non-hybridizable-non-complementary regions in the target nucleic acid sequence are selected in the step (b) such that they comprise no nucleotides involved in Watson-Crick base pairing with the first tagging part. Alternatively, the regions may be selected such that they comprise 1 or less, 2 or less, or 3 or less nucleotides involved in Watson-Crick base pairing with the first tagging part. Alternatively, the regions may be selected such that they comprise 1, 2 or 3 nucleotides involved in Watson-Crick base pairing with the first tagging part.

According to an embodiment, the predetermined threshold value to be applied to the non-complementarity level to the first tagging part is determined such that the selected one or more non-hybridizable-non-complementary regions comprise 0, 1 or less, 2 or less, or 3 or less of nucleotides involved in Watson-Crick base pairs with the first tagging part.

According to an embodiment, the non-complementarity level of the selected at least one region in a target nucleic acid sequence to the second tagging part is independently evaluated by using an independent criterion or predetermined threshold value criterion for the second tagging part.

According to an embodiment, the one or more non-hybridizable-non-complementary regions in the target nucleic acid sequence are selected in the step (b) such that they are Watson-Crick base paired with 80% or less, 70% or less, 60% or less, 50% or less, 40% or less, 30% or less, 20% or less, or 10% or less of the total nucleotides of the second tagging part.

According to an embodiment, the predetermined threshold value to be applied to the non-complementarity level to the second tagging part is determined such that the selected one or more non-hybridizable-non-complementary regions are Watson-Crick base paired with 80% or less, 70% or less, 60% or less, 50% or less, 40% or less, 30% or less, 20% or less, or 10% or less of the total nucleotides of the second tagging part.

According to an embodiment, when the first tagging part has a nucleotide involved in Watson-Crick base pairs with the selected at least one region, the region in the target nucleic acid sequence is selected such that the Watson-Crick base paired nucleotide of the first tagging part is not located at a position of 0-1 nucleotide apart from the nucleotide of the first tagging part immediately adjacent to the targeting portion.

In the present invention, 'the non-complementarity level' may be expressed as a value representing binding unfavorability between nucleotide bases. For example, although the base pairs (AG), (AC) and (AA) are all expressed as non-complementary base pairs, their unfavorabilities based on binding force are different from each other. The term "non-complementarity level" may be expressed particularly by using the unfavorability based on such binding force.

Since the descriptions for "unfavorability", "favorability", "interpretation of binding force calculation results", "calculation of binding force", "giving score of unfavorability or favorability" and "calculation of unfavorability or favorability" in the second aspect of the present invention are the same as those of the first aspect of the present invention, the common descriptions between them are omitted in order to avoid undue redundancy leading to the complexity of this specification.

The higher the non-complementarity level, the more likely it is to become the non-hybridizable-non-complementary region. The non-complementarity level may be quantified (e.g., numericized) using a variety of methods. Particularly, the non-complementarity level used in the present invention is a quantified or numericized non-complementarity level.

The non-hybridizable-non-complementary regions to the tagging portion are selected for sequences with non-complementarity levels satisfying a predetermined threshold value criterion. The threshold value may be determined empirically or theoretically. According to an embodiment, the non-complementarity level may be obtained or evaluated by the unfavorability between the nucleotide bases. According to an embodiment, when the binding force between a base pair is lower, a higher score is given, and the score is used as the unfavorability, and when the non-complementarity level is calculated using the unfavorability, the selection of the non-hybridizable-non-complementary target nucleic acid regions to the tagging portion is performed by selecting regions having the non-complementarity level that is equal to or larger than the predetermined threshold value.

Alternatively, when the binding force is lower, a lower score is given, and the score may be used as the unfavorability. When the non-complementarity level is calculated using the unfavorability to which the score is given in this way, the selection of the non-hybridizable-non-complementary regions to the tagging portion is performed by selecting regions having the non-complementarity level that is smaller than or equal to the predetermined threshold value.

As the alternative example, 'when the binding force is lower, a lower score is given, and the score may be used as the unfavorability' may be expressed as 'when the binding force is lower, a lower score is given, and the score may be used as the favorability'. The non-complementarity level may be calculated using the favorability to which the score is given in this way. In this case, the selection of the non-hybridizable-non-complementary regions to the tagging portion is performed by selecting regions having the non-complementarity level that is smaller than or equal to the predetermined threshold value.

Alternatively, 'when the binding force is lower, a higher score is given, and the score may be used as the unfavorability' may be expressed as 'when the binding force is lower, a higher score is given, and the score may be used as the favorability'. The non-complementarity level may be calculated using the favorability to which the score is given in this way. In this case, the selection of the non-hybridizable-non-complementary regions to the tagging portion is performed by selecting regions having the non-complementarity level that is equal to or larger than the predetermined threshold value.

According to an embodiment of the present invention, the non-complementarity level may be provided by scores given depending on unfavorability of the bonds between nucleotide bases A, T, G and C. Particularly, the non-complementarity level is the sum or the product of the scores given depending on unfavorability of the bonds between nucleotide bases A, T, G and C.

The non-complementarity level to the entire tagging portion is obtained or provided by the scores given to the base pairs between the tagging portion and a nucleotide sequence located on opposite to the tagging portion. The score is named as "a tagging portion score".

The non-complementarity level to the first tagging part is obtained or provided by the scores given to the base pairs between the first tagging part and a nucleotide sequence located on opposite to the first tagging part. The score is named as "a first tagging part score".

The non-complementarity level to the second tagging part is obtained or provided by the scores given to the base pairs between the second tagging part and a nucleotide sequence located on opposite to the second tagging part. The score is named as "a second tagging part score".

For example, where the sequence of the first tagging part is 5'-AGTC-3' and the sequence of the region in the target nucleic acid sequence located on opposed to the first tagging part is 3'-GGTA-5', the unfavorability of the first tagging part calculated by the first approach becomes 1.0+1.3+1.3+1.0=4.6. When the predetermined threshold value is 3.0, the 4.6 point is more than the threshold value and therefore 3'-GGTA-5' may be selected as the non-hybridizable-non-complementary sequence to the tagging portion.

Since the description for "ways to give a score to a bond between nucleotide base pairs" in the second aspect of the present invention is the same as that of the first aspect of the present invention, the common descriptions between them are omitted in order to avoid undue redundancy leading to the complexity of this specification.

According to an embodiment, the non-complementarity level between the entire sequence of the tagging portion and the region located on the opposite side in the target nucleic acid sequence is obtained by unfavorability between nucleotide bases. According to an embodiment, the unfavorability is a weighted unfavorability in which weighting values are assigned to an oppositely located target region to the tagging portion in a successively increasing manner from an oppositely located target location to a location of the second tagging part most distant from the targeting portion to an oppositely located target location to a location of the first tagging part most adjacent to the targeting portion.

For example, when the tagging portion is composed of 12 nucleotides, the weighting values of "1, 4, 9, 16, 25, 36, 49, 64, 81, 100, 121 and 144" or "2, 3, 4, 6, 9, 12, 14, 21, 28, 30, 45 and 60" are given from an oppositely located target location to a location of the second tagging part most distant from the targeting portion to an oppositely located target location to a location of the first tagging part most adjacent to the targeting portion and the unfavorability of the entire sequence of the tagging portion may be calculated using the weighting values and the scores as unfavorability of base pairs (e.g., multiply the weighting values by the unfavorability score), thereby obtaining the non-complementarity level.

When the regions in a plurality of target nucleic acid sequences are selected, the weighting approaches described above may be also useful to rank the selected regions.

According to an embodiment, the non-hybridizable-non-complementary regions in the target nucleic acid sequence to the nucleotide sequence for the tagging portion is selected by selecting the regions that comprise no nucleotides involved in Watson-Crick base pairing with the first tagging part and then considering ranking of scores given to bonds between nucleotide base pairs to obtain the non-complementarity level to the entire tagging portion.

In the second aspect of this invention, the non-complementarity level is described to be evaluated and scored for a region of a target nucleic acid sequence located oppositely to a tagging portion, thereby selecting a non-hybridizable-non-complementary region based on the non-complementarity level. It will be understood by one of skill in the art that the non-complementarity level may be evaluated and scored for a tagging portion located oppositely to a region of a target nucleic acid sequence, thereby selecting a non-hybridizable-non-complementary region based on the non-complementarity level of the tagging portion. Therefore, one of skill in the art will understand that all modifications in assigning a non-complementarity level fall within the scope of the second aspect so long as they select a non-hybridizable-non-complementary region in a target nucleic acid sequence rather than a tagging portion based on evaluation of the non-complementarity level.

Step (c): Selection of a Nucleotide Sequence for the Targeting Portion (230)

Following the step (b), a nucleotide sequence for the targeting portion is selected by (i) selecting a nucleotide sequence with a predetermined length in the target nucleic acid sequence that is adjacent to the non-hybridizable-non-complementary region to the nucleotide sequence of the tagging portion and (ii) selecting a hybridizable-complementary nucleotide sequence to the selected nucleotide sequence in the target nucleic acid as the nucleotide sequence for the targeting portion.

A nucleotide sequence of a region adjacent to the non-hybridizable-non-complementary region to the nucleotide sequence of the tagging portion selected in the step (b) is used.

The region adjacent to the non-hybridizable-non-complementary region to the nucleotide sequence of the tagging portion may exist on both sides of the non-hybridizable-non-complementary region, and the position of the adjacent region may be determined depending on whether the tagging portion is located at a 5' or 3' end portion at the tagging oligonucleotide.

The 5'-tagging oligonucleotide comprises in a 5' to 3' direction, the tagging portion and the targeting portion. The target nucleic acid sequence hybridized with the 5'-tagging oligonucleotide comprises in a 3' to 5' direction, the non-hybridizable-non-complementary region and the adjacent region. The 3'-tagging oligonucleotide comprises in a 5' to 3' direction, the targeting portion and the tagging portion. The target nucleic acid sequence hybridized with the 3'-tagging oligonucleotide comprises in a 3' to 5' direction, the adjacent region and the non-hybridizable-non-complementary region.

The region adjacent to the non-hybridizable-non-complementary region is a region located on the opposite side of the targeting portion of the tagging oligonucleotide and a nucleotide sequence for the targeting portion may be determined using a nucleotide sequence of the adjacent region.

According to an embodiment of the present invention, a nucleotide sequence having a predetermined length among nucleotide sequences of the region adjacent to the non-hybridizable-non-complementary region is selected. Particularly, the predetermined length of the nucleotide sequence is 6-50 nucleotides. More particularly, the predetermined length is 6-40, 6-35, 6-30, 10-50, 10-40, 10-35, 10-30, 15-50, 15-40, 15-35, 15-30, 20-50, 20-40, 20-35, or 20-30 nucleotides.

The nucleotide sequence of the region adjacent to the non-hybridizable-non-complementary region may have various lengths. The predetermined length may be one, two or more lengths.

Where the nucleotide sequence of the region adjacent to the non-hybridizable-non-complementary region is selected, a hybridizable-complementary nucleotide sequence thereto may be selected as the targeting portion sequence of the tagging oligonucleotide.

According to one embodiment of the present invention, the nucleotide sequence complementary to the nucleotide sequence of the region adjacent to the non-hybridizable-non-complementary region is selected as the nucleotide sequence of the targeting portion. According to one embodiment, some non-complementary nucleotides may be contained in targeting portion so long as the targeting portion may be hybridized with the target nucleic acid sequence. For example, the number of non-complementary nucleotides may be 1, 2, 3 or 4, 5 or more. Alternatively, a non-natural nucleotide comprising a non-natural base or nucleotide backbone may be contained. For example, the number of non-natural nucleotides may be 1, 2, 3 or 4, 5 or more.

Since the descriptions for "selection of the nucleotide sequence of the targeting portion" in the second aspect of the present invention are the same as those of the first aspect of the present invention, the common descriptions between them are omitted in order to avoid undue redundancy leading to the complexity of this specification.

According to an embodiment, the target nucleic acid sequence is a nucleic acid sequence to be amplified and the selections in the steps (b) and (c) is performed within an amplification region of the target nucleic acid sequence.

Step (d): Preparation of the Tagging Oligonucleotide (240)

The tagging oligonucleotide comprising the nucleotide sequence of the tagging portion provided in the step (a) and the nucleotide sequence of the targeting portion selected in the step (c) is prepared.

Since the descriptions for "preparation of the tagging oligonucleotide" in the second aspect of the present invention are the same as those of the first aspect of the present invention, the common descriptions between them are omitted in order to avoid undue redundancy leading to the complexity of this specification.

According to an embodiment of the present invention, the target nucleic acid sequence comprises a plurality of nucleic acid sequences for a sequence exhibiting genetic diversity, the tagging oligonucleotide is used for detection of all of the plurality of target nucleic acid sequences, and the non-hybridizable-non-complementary nucleotide sequence regions in the step (b) are selected in the plurality of target nucleic acid sequences such that their non-complementarity levels to the nucleotide sequence for the tagging portion all satisfy a predetermined threshold value criterion and a targeting portion of the tagging oligonucleotide has a single type sequence.

Since the description for "genetic diversity" in the second aspect of the present invention is the same as that of the first aspect of the present invention, the common descriptions between them are omitted in order to avoid undue redundancy leading to the complexity of this specification.

Storage Medium, Device and Program

In another aspect of this invention, there is provided a computer readable storage medium containing instructions to configure a processor to perform a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, the method comprising:

(a) providing a nucleotide sequence for the tagging portion; wherein the tagging portion comprises a first tagging part adjacent to the targeting portion and a second tagging part adjacent to the first tagging part;

(b) selecting in the target nucleic acid sequence one or more non-hybridizable-non-complementary regions to the nucleotide sequence for the tagging portion by (i) selecting at least one region in the target nucleic acid sequence and (ii) evaluating a non-complementarity level of the selected at least one region to the nucleotide sequence for the tagging portion;

(c) selecting a nucleotide sequence for the targeting portion by (i) selecting a nucleotide sequence with a predetermined length in the target nucleic acid sequence that is adjacent to the non-hybridizable-non-complementary region to the nucleotide sequence of the tagging portion and (ii)

selecting a hybridizable-complementary nucleotide sequence to the selected nucleotide sequence in the target nucleic acid as the nucleotide sequence for the targeting portion; and (d) preparing the tagging oligonucleotide comprising the nucleotide sequence of the tagging portion provided in the step (a) and the nucleotide sequence of the targeting portion selected in the step (c).

In still another aspect of this invention, there is provided a computer program to be stored on a computer readable storage medium, to configure a processor to perform a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, the method comprising:

(a) providing a nucleotide sequence for the tagging portion; wherein the tagging portion comprises a first tagging part adjacent to the targeting portion and a second tagging part adjacent to the first tagging part;

(b) selecting in the target nucleic acid sequence one or more non-hybridizable-non-complementary regions to the nucleotide sequence for the tagging portion by (i) selecting at least one region in the target nucleic acid sequence and (ii) evaluating a non-complementarity level of the selected at least one region to the nucleotide sequence for the tagging portion;

(c) selecting a nucleotide sequence for the targeting portion by (i) selecting a nucleotide sequence with a predetermined length in the target nucleic acid sequence that is adjacent to the non-hybridizable-non-complementary region to the nucleotide sequence of the tagging portion and (ii) selecting a hybridizable-complementary nucleotide sequence to the selected nucleotide sequence in the target nucleic acid as the nucleotide sequence for the targeting portion; and (d) preparing the tagging oligonucleotide comprising the nucleotide sequence of the tagging portion provided in the step (a) and the nucleotide sequence of the targeting portion selected in the step (c).

In another aspect of this invention, there is provided a device for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, comprising (a) a computer processor, and (b) a computer readable storage medium of the present method coupled to the computer processor.

Since the storage medium, the device and the computer program of the prevent invention are intended to perform the present methods described hereinabove in a computer, the common descriptions between them are omitted in order to avoid undue redundancy leading to the complexity of this specification.

Since the descriptions for "the program instructions", "a processor", "the types of the computer readable storage medium", "ways of providing the tagging oligonucleotide", "the instructions to configure the processor" and "the computer processor" in the second aspect of the present invention are the same as those of the first aspect of the present invention, the common descriptions between them are omitted in order to avoid undue redundancy leading to the complexity of this specification.

Advantageous Effects of Invention

The features and advantages of this invention are summarized as follows:

(a) In conventional methods for providing tagging oligonucleotides, the tagging portion is designed such that its entire sequence is non-complementary to a target nucleic acid sequence. Unlikely, the first aspect of the present invention selects sequences of the tagging portion by the independent non-complementarity level of its partial sequence, i.e., the first tagging part.

(b) By analyzing exquisitely the non-complementarity level of the first tagging part, the first aspect of the present invention permits to more efficiently and easily select a suitable tagging sequence among a multitude of sequences generated theoretically.

(c) Conventional methods for detecting target nucleic acid sequences using the tagging oligonucleotide and the third template which hybridizes with its tagging portion generally first select a nucleotide sequence of the targeting portion to be hybridized with the target nucleic acid sequence, and then a nucleotide sequence of the tagging portion is selected in considering a nucleotide sequence located on opposite to the tagging portion. In this case, because the sequence of the tagging portion is designed differently depending on hybridization positions of the targeting portion with reference to the target nucleic acid sequence and therefore the third template to be hybridized with the tagging portion has to be newly designed, the conventional methods are cost-ineffective and time-ineffective. The second aspect of the present invention may solve the problems of conventional methods by firstly selecting the nucleotide sequence for the tagging portion and then selecting the nucleotide sequence for the targeting portion.

(d) Since the second aspect of the present invention uses the tagging portion of a predetermined nucleotide sequence, the artificial template that hybridizes with the tagging portion may be supplied in a ready-made manner, and even one type of the artificial template allows for the detection of a variety of nucleic acid sequences. In addition, since a single type of a labeled artificial template hybridizable with the predetermined tagging portion may be prepared and kept before starting experiments, various target nucleic acid sequences may be efficiently detected in a real-time manner while minimizing the time and economic cost.

(e) According an embodiment of the second aspect of the present invention, the non-hybridizable-non-complementary region in the target nucleic acid sequence may be more efficiently selected by applying independent different non-complementary levels to the second tagging part and the first tagging part as well as by analyzing a non-complementary level to the entire tagging portion.

(f) When the first and second aspects of the present invention are implemented by a computer program, tagging oligonucleotides having suitable tagging sequences may be very efficiently and quickly prepared.

BRIEF DESCRIPTION OF DRAWINGS

FIG. 1 is a flow diagram representing a process in accordance with a representative embodiment of the first aspect of the present invention.

FIG. 2 is a flow diagram showing a process in accordance with a representative embodiment of the second aspect of the present invention.

MODE FOR THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Preparation of Tagging Oligonucleotides for the Detection of Multiple F Genes of Human Metapneumovirus Tagging oligonucleotides for the detection of multiple F genes of human metapneumovirus having genetic diversity were prepared in accordance with the first aspect of the present invention. The tagging oligonucleotides prepared in the Example are a 5'-tagging oligonucleotide comprising in the 5' to 3' direction, a tagging portion and a targeting portion, which serve as probes.

Determination of a Targeting Portion Sequence and Classification of an Opposite Target Nucleic Acid Sequence to the Tagging Portion A plurality of F genes of human metapneumovirus were aligned to find a conserved region and then the sequence of the targeting portion of the tagging oligonucleotide to be hybridized with the conserved region was determined:

5'-CCTGCAGATGTTGGCATGT-3'.     (SEQ ID NO: 1)

Then, the sequence of the targeting portion was searched against all sequences of the F genes in the GenBank database to extract sequences of the F genes comprising regions with homology to the sequence of the targeting portion. In the extracted target nucleic acid sequences, nucleotide sequences located on opposite to a 5'-tagging portion were collected and classified based on nucleotide sequences with which the sequence of the targeting portion was hybridized (see Table 1).

TABLE 1

| IN-DEX | Opposite SEQ[1] (3' to 5') | Sequence Complementary to Opposite SEQ (5' to 3') | Sequence Count No. |
|---|---|---|---|
| 1 | 3'-TCAAAATAGACA-5' (SEQ ID NO: 2) | 5'-AGTTTTATCTGT-3' (SEQ ID NO: 3) | 444 |
| 2 | 3'-TCAAAATAAACA-5' (SEQ ID NO: 4) | 5'-AGTTTTATTTGT-3' (SEQ ID NO: 5) | 237 |
| 3 | 3'-TCAAAATAGACG-5' (SEQ ID NO: 6) | 5'-AGTTTTATCTGC-3' (SEQ ID NO: 7) | 143 |
| 4 | 3'-TTAAAATAAACA-5' (SEQ ID NO: 8) | 5'-AATTTTATTTGT-3' (SEQ ID NO: 9) | 29 |
| 5 | 3'-TTAAAATAGACA-5' (SEQ ID NO: 10) | 5'-AATTTTATCTGT-3' (SEQ ID NO: 11) | 15 |
| 6 | 3'-TCGAAATAGACA-5' (SEQ ID NO: 12) | 5'-AGCTTTATCTGT-3' (SEQ ID NO: 13) | 10 |
| 7 | 3'-TCAAAATAAACG-5' (SEQ ID NO: 14) | 5'-AGTTTTATTTGC-3' (SEQ ID NO: 15) | 6 |
| 8 | 3'-TCGAAATAGACG-5' (SEQ ID NO: 16) | 5'-AGCTTTATCTGC-3' (SEQ ID NO: 17) | 5 |
| 9 | 3'-TCAAAATAGACT-5' (SEQ ID NO: 18) | 5'-AGTTTTATCTGA-3' (SEQ ID NO: 19) | 1 |
| 10 | 3'-TCCAAATAAACA-5' (SEQ ID NO: 20) | 5'-AGGTTTATTTGT-3' (SEQ ID NO: 21) | 1 |

[1] Oppsite SEQ means a nucleotide sequence opposite to a tagging portion of the tagging oligonucleotide.

As shown in Table 1, the nucleotide sequences located on opposite to the 5'-tagging portion can be classified into 10 types and the number of the F genes having genetic diversity belonging to each group is indicated in the rightmost column of Table 1.

First Selection

The sequences suitable for a 5'-tagging portion were selected from a tagging sequence database in taking into account the opposite nucleotide sequences to the 5'-tagging portion searched and classified above.

The criteria for the first selection are as follows: (i) inclusion of 12 mer in length, (ii) exclusion of sequences comprising a mononucleotide run sequence, AAAA, TTTT, CCCC and GGGG, (iii) inclusion of a sequence having 5-9 G/C; (iv) exclusion of a sequence in which G and/or C is consecutively located in the number of 8 or more in the 3'-end part of the tagging portion, (v) when the 5'-tagging portion forms a homodimer, exclusion of a sequence in which the number of nucleotides involved in the formation of the homodimer is 8 or more, and (vi) when the 5'-tagging portion forms a homodimer, exclusion of a sequence in which the number of consecutive nucleotides involved in the formation of the homodimer is 7 or more.

The number of tagging candidate sequences selected by the first criteria was about 3,000,000.

Second Selection

Afterwards, the tagging candidate sequences selected were sorted according to the second selection criteria to obtain approximately 30,000 tagging candidate sequences. The second selection criteria are applied for a first tagging part of the tagging portion. The second selection criteria are as follows: (i) inclusion of a sequence in which a first tagging part score average of the first tagging part is 4.0 or more, (ii) when the tagging portion forms the 5'-tagging oligonucleotide together with the targeting portion, exclusion of a sequence of the first tagging part rendering ΔG value for a hairpin structure of the 5'-tagging oligonucleotide to become −5 kcal/mol or less, and (iii) inclusion of a sequence in which a pass ratio of the first tagging part is 95% or more (based on a first tagging part score as a predetermined threshold value criterion 4.0).

When a binding force of base pairs was lower, a higher score was given. The score was used as unfavorability: 1.3 points for (AA), (TT), (GG) and (CC) base pairs, 1.0 point for (TC), (AG), (AC) and (TG) base pairs, 0 point for (AT), (TA), (GC) and (CG) base pairs.

The unfavorability was used to calculate first tagging part scores for nucleotide sequences of the first tagging part.

In the above-described expression indicating the base pair score for each base pair, the base pair in the parentheses represents a base pair of two opposite nucleotides in a double stranded nucleic acid sequence. One of the two opposite nucleotides is in a 5' to 3' direction and the other in a 3' to 5' direction. When such base pair expression is used, the nucleotide sequence of the 5'-tagging portion and the nucleotide sequence located on opposite to the 5'-tagging portion (Opposite SEQ in Table 1) were aligned and the first tagging part score was calculated. Alternatively, a nucleotide in a 3' to 5' direction of the base pair in the parentheses may be expressed as its complementary bases. For example, the alternative gives 1.3 points for (AT), (TA), (GC) and (CG) base pairs, 1.0 point for (TG), (AC), (AG) and (TC) base pairs, and 0 point for (AA), (TT), (GG) and (CC) base pairs. When such alternative base pair expression is used, the nucleotide sequence of the 5'-tagging portion is used as it is and the opposite sequence (e.g., Opposite SEQ in Table 1) is used after replacing with its complementary sequence (e.g., Sequence Complementary to Opposite SEQ in Table 1). The two sequences are aligned to calculate the first tagging part score.

The first tagging part score average and pass ratio of the first tagging part of each of the tagging candidate sequences were calculated.

Then, a non-complementarity level of an entire sequence of each of the tagging candidate sequences was calculated. The non-complementarity level was calculated using the base pair scores applied to the first tagging part score. In addition, the non-complementarity level of the entire sequence of the tagging portion was calculated by giving the weighting values of "2, 3, 4, 6, 9, 12, 14, 21, 28, 30, 45 and 60" from a 5'-end of the second tagging part to a 3'-end of the first tagging part.

The top 100 tagging candidate sequences were selected in taking into consideration the pass ratio, the non-complementarity level of the entire sequence of the tagging portion, the first tagging part score average and the hairpin structure-forming ΔG value. Among these, the top 10 tagging candidate sequences are as follows:

| Sequence | SEQ ID NO |
|---|---|
| AAGGGACAGACG, | (SEQ ID NO: 22) |
| ATAGGGCAGACG, | (SEQ ID NO: 23) |
| AAG-GAGCAGACG, | (SEQ ID NO: 24) |
| AAGAGGCAGACG, | (SEQ ID NO: 25) |
| AACGGGTAGACG, | (SEQ ID NO: 26) |
| AAGGGATGGACG, | (SEQ ID NO: 27) |
| ATAGGGTGGACG, | (SEQ ID NO: 28) |
| AAAGGGCAGACG, | (SEQ ID NO: 29) |
| AACGGACAGACG, and | (SEQ ID NO: 30) |
| ATAGGACGGACG. | (SEQ ID NO: 31) |

Third Selection

The third selection was performed on the selected tagging candidate sequences. The criteria for the third selection are as follows: (i) when the tagging portion forms a heterodimer with a primer for amplification of the target nucleic acid sequence, exclusion of a sequence in which the number of nucleotides forming base pairs in the tagging portion is 9 mer or more; and (ii) when the tagging portion forms a heterodimer with a primer for amplification of the target nucleic acid sequence, exclusion of a sequence in which the ratio of nucleotides forming consecutive base pairs in the tagging portion is 8 mer or more.

By the third selection, the tagging candidate sequence "ATAGGGCAGACG (SEQ ID NO:23)" was excluded because it was analyzed to involve 12-mer nucleotides in the formation of the heterodimer. The nine tagging candidate sequences were selected.

Finally, nine tagging oligonucleotides each was prepared to comprise one of nine tagging candidate sequences as the 5'-tagging portion and the sequence of SEQ ID NO:1 as the 3'-targeting portion.

The nine 5'-tagging oligonucleotides finally prepared were analyzed whether they can serve as probes for detection of the F gene of human metapneumovirus in the PTOCE method (see WO 2012/096523) involving amplification of target and cleavage of probe (5'-tagging oligonucleotide).

Viral total RNA was extracted by using the RNAzol B method according to the manufacturer's protocol (RNAzol LS; Tel-Test, Inc.). Reverse transcription reaction was performed to synthesize cDNA using the viral RNA for 1.5 hr at 42° C. in a reaction volume of 20 μl composed of the followings: 5 μl of total RNA (approximately 100 ng), 4 μl of 5× reaction buffer (Invitrogen, USA), 5 μl of dNTPs (each 5 mM), 2 μl of 10 μM random hexadeoxynuclotides, 0.5 μl of RNase inhibitor (40 units/0, Promega), and 1 μl of Moloney murine leukemia virus reverse transcriptase (200 units/0, Promega).

The reactions for the PTOCE method were conducted in the final volume of 20 μl containing 2 pmole of the synthesized cDNA as templates, 10 pmole of upstream primer, 5 pmole of the 5'-tagging oligonucleotide as the PTO, 2 pmole of the CTO, 10 μl of 2× Master Mix containing 2.5 mM $MgCl_2$, 200 μM of dNTPs and 1.6 units of H-Taq DNA polymerase (Solgent, Korea); a tube containing the reaction mixture was placed on the real-time thermocycler (CFX96, Bio-Rad); the reaction mixture was denatured for 15 min at 95° C. and subjected to 60 cycles of 30 sec at 95° C., 60 sec at 60° C. and 30 sec at 72° C. Signals at 60° C. of each cycle were detected to determine the presence or absence of the F gene of human metapneumovirus.

The reaction results according to the PTOCE method showed that target signals (around C, 28-33) were successfully detected in the presence of the target nucleic acid sequence, demonstrating that the tagging oligonucleotides prepared in the Example works well as probes.

Example 2: Preparation of Tagging Oligonucleotides for the Detection of *Mycoplasma pneumoniae*

Tagging oligonucleotides used for detecting a genomic DNA of *Mycoplasma pneumoniae* were prepared in accordance with the second aspect of the present invention. The tagging oligonucleotides prepared in this Example are a 5'-tagging oligonucleotide comprising in a 5' to 3' direction the tagging portion and the targeting portion, which serve as probes.

Preparation of Tagging Portion

The 948-2552 nucleotide sequence of GenBank Accession id NZ_KQ758443.1 was used as a target nucleic acid sequence. Two sequences as a tagging portion were provided from a tagging portion candidate database prepared in no consideration of the target nucleic acid sequence, and a primer pair was designed to amplify the target sequence (see Table 2).

TABLE 2

| Name | Type | Sequence (5' to 3') | SEQ ID NO |
|---|---|---|---|
| MP_F | Primer | CAGCTCAATCAGGAATGGTTTCAC | SEQ ID NO: 32 |

TABLE 2-continued

| Name | Type | Sequence (5' to 3') | SEQ ID NO |
|---|---|---|---|
| MP_R | Primer | CTCAGTTTGCCCATTGTTTAACCA | SEQ ID NO: 33 |
| Tag-1 | Tagging portion | GTCGTACGCGAT | SEQ ID NO: 34 |
| Tag-2 | Tagging portion | CACGCGACGATT | SEQ ID NO: 35 |

Searching and Selection of Non-Hybridizable-Non-Complementary Regions in the Target Sequence The non-hybridizable-non-complementary regions to the Tag-1 or Tag-2 were searched and extracted by sliding a sequence window (i.e., a sequence of Tag-1 or Tag-2) nucleotide by nucleotide in a 3' to 5' direction along the target nucleic acid sequence. The non-hybridizable-non-complementary regions were extracted from each of both strands of the target nucleic acid sequence (a forward strand and a reverse strand).

The 8-mer sequence from the 5'-end of the tagging portion were used as a second tagging part and the remaining 4-mer sequence were used as a first tagging part. The regions (12-mer length) in the target nucleic acid sequence were extracted where they satisfy a criterion that there are at least four match nucleotides with the second tagging part and are no match nucleotides with the first tagging part.

The non-complementarity levels of the non-hybridizable-non-complementary regions to the entire sequence of the tagging portion were obtained by scoring binding force of base pairs between the nucleotide sequence of the tagging portion and the nucleotide sequence of the extracted regions.

When the binding force of base pairs was lower, a higher score was given. The score was used as unfavorability: 1.3 points for (AA), (TT), (GG) and (CC) base pairs, 1.0 point for (TC), (AG), (AC) and (TG) base pairs, 0 point for (AT), (TA), (GC) and (CG) base pairs.

The unfavorability was used to calculate (i) scores for the non-hybridizable-non-complementary regions or (ii) scores for the tagging portion located oppositely to the non-hybridizable-non-complementary regions. In the calculation of (i), the weighting values were given as "2, 3, 4, 6, 9, 12, 14, 21, 28, 30, 45 and 60" from a nucleotide of the target region located oppositely to the 5'-end of the second tagging part to a nucleotide of the target region located oppositely to the 3'-end of the first tagging part. In the calculation of (ii), the weighting values were given as "2, 3, 4, 6, 9, 12, 14, 21, 28, 30, 45 and 60" from the 5'-end of the second tagging part to the 3'-end of the first tagging part.

The non-hybridizable-non-complementary regions were selected by using the scores.

Selection of the Targeting Portion

The nucleotide sequences of 30-38 nucleotides in length were extracted from nucleotide sequences adjacent to the non-hybridizable-non-complementary regions selected. The nucleotide sequences complementary to the extracted nucleotide sequences were used as nucleotide sequences of candidate targeting portions.

Among the candidate targeting portions, we selected targeting portions satisfying criteria such that (i) the 5' end nucleotide of the selected targeting portion is G or C and (ii) a $T_m$ value of the selected targeting portion is 72-78° C. The $T_m$ value is a criterion ensuring that the $T_m$ value of the selected targeting portion is 10-15° C. higher than that of the primers in Table 2.

Preparation of Tagging Oligonucleotides

The tagging oligonucleotides were prepared by combining Tag-1 or Tag-2 with one of the selected targeting portions. The tagging oligonucleotides prepared were sorted and ranked by a length (preference to shorter length), a hairpin structure-forming ΔG value (preference to higher ΔG value) and a number of consecutive nucleotides forming a homodimer (preference to less number). High-ranked tagging oligonucleotides were selected (Table 3).

TABLE 3

| No | STRAND | TAG ID | TAG Mis-Match[1] | Sequence of targeting portion (5' to 3') | Length[2] | ΔG[3] | MaxCon Dimer[4] |
|---|---|---|---|---|---|---|---|
| 1 | Forward | Tag-1 | 9 | GAACAAGCC TTGGACGCT GGTACGCA (SEQ ID NO: 36) | 26 | −0.9 | 10 |
| 2 | Reverse | Tag-1 | 10 | GCTCACCGT TCACGACAC AAAGGCACG (SEQ ID NO: 37) | 27 | −0.6 | 10 |
| 3 | Forward | Tag-1 | 12 | GGTACCCGT GCCTTTGTG TCGTGAACG (SEQ ID NO: 38) | 27 | −0.6 | 10 |
| 4 | Reverse | Tag-1 | 10 | GCTTAAGCA CGCCACTAC CCCAAGCTT (SEQ ID NO: 39) | 27 | −0.7 | 10 |
| 5 | Forward | Tag-1 | 9 | GAACAAGCC TTGGACGCT GGTACGCAA (SEQ ID NO: 40) | 27 | −0.9 | 10 |
| 6 | Forward | Tag-2 | 11 | CAAATCCTG GTGGGTGAC AAACGCTTG (SEQ ID NO: 41) | 27 | 1.1 | 4 |
| 7 | Forward | Tag-2 | 11 | CAAATCCTG GTGGGTGAC AAACGCTTG T (SEQ ID NO: 42) | 28 | 0.8 | 4 |
| 8 | Forward | Tag-2 | 12 | CCCCAAAGT GTGTCGACT GCTAGTGCC G (SEQ ID NO: 43) | 28 | 0.7 | 6 |

[1] the number of mismatched nucleotides of Tag-1 or Tag-2 to the non-hybridizable-non-complementary region selected;
[2] the length of targeting portions;
[3] ΔG value (kcal/mol) for a hairpin structure of tagging oligonucleotides;
[4] the maximum number of consecutive nucleotides of tagging oligonucleotides involved in the formation of homodimer.

Among the eight tagging oligonucleotides selected, the tagging oligonucleotides numbered 6-8 were analyzed whether they can serve as probes for detection of the genomic DNA of *Mycoplasma pneumoniae* in the PTOCE method (see WO 2012/096523) involving amplification of target and cleavage of probe (tagging oligonucleotide).

The reactions for the PTOCE method were conducted in the final volume of 20 μl containing 100 pg of the genomic DNA as templates, 10 pmole of upstream primer, 5 pmole of the tagging oligonucleotide as the PTO, 2 pmole of the CTO, 10 μl of 2× Master Mix containing 2.5 mM $MgCl_2$, 200 μM of dNTPs and 1.6 units of H-Taq DNA polymerase (Solgent, Korea); a tube containing the reaction mixture was placed on the real-time thermocycler (CFX96, Bio-Rad); the reaction mixture was denatured for 15 min at 95° C. and subjected to 60 cycles of 30 sec at 95° C., 60 sec at 60° C. and 30 sec at 72° C. Signals at 60° C. of each cycle were detected to determine the presence or absence of *Mycoplasma pneumoniae*.

The reaction results according to the PTOCE method showed that target signals (around C, 29-31) were successfully detected in the presence of the target nucleic acid sequence, demonstrating that the tagging oligonucleotides prepared in the Example works well as probes.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, comprising:
   (a) selecting the hybridizable-complementary nucleotide sequence to the target nucleic acid sequence for the targeting portion and the non-hybridizable-non-complementary nucleotide sequence to the target nucleic acid sequence for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the target nucleic acid sequence; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and
   (b) preparing the tagging oligonucleotide comprising (i) the targeting portion comprising the selected hybridizable-complementary nucleotide sequence and (ii) the tagging portion comprising the selected non-hybridizable-non-complementary nucleotide sequence.

2. A method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, comprising:
   (a) providing a nucleotide sequence for the tagging portion; wherein the tagging portion comprises a first tagging part adjacent to the targeting portion and a second tagging part adjacent to the first tagging part;
   (b) selecting in the target nucleic acid sequence one or more non-hybridizable-non-complementary regions to the nucleotide sequence for the tagging portion by (i) selecting at least one region in the target nucleic acid sequence and (ii) evaluating a non-complementarity level of the selected at least one region to the nucleotide sequence for the tagging portion;
   (c) selecting a nucleotide sequence for the targeting portion by (i) selecting a nucleotide sequence with a predetermined length in the target nucleic acid sequence that is adjacent to the non-hybridizable-non-complementary region to the nucleotide sequence of the tagging portion and (ii) selecting a hybridizable-complementary nucleotide sequence to the selected nucleotide sequence in the target nucleic acid as the nucleotide sequence for the targeting portion; and
   (d) preparing the tagging oligonucleotide comprising the nucleotide sequence of the tagging portion provided in the step (a) and the nucleotide sequence of the targeting portion selected in the step (c).

3. The method according to claim 1, wherein the non-hybridizable-non-complementary nucleotide sequence in the tagging portion, the hybridizable-complementary nucleotide sequence in the targeting portion, or the non-hybridizable-non-complementary nucleotide sequence in the tagging portion and the hybridizable-complementary nucleotide sequence in the targeting portion is selected or provided from a pre-established dataset of tagging portion candidates or a pre-established dataset of targeting portion candidates.

4. The method according to claim 2, wherein the evaluation of the non-complementarity level of the selected at least one region in the target nucleic acid sequence in the step (b) is performed by evaluating the non-complementarity level to an entire sequence of the nucleotide sequence for the tagging portion.

5. The method according to claim 2, wherein the evaluation of the non-complementarity level of the selected at least one region in the target nucleic acid sequence in the step (b) is performed by evaluating the non-complementarity level to the first tagging part of the nucleotide sequence for the tagging portion in an independent manner.

6. The method according to claim 1, wherein the non-complementarity level is evaluated by unfavorability between nucleotide bases.

7. The method according to claim 1, wherein the non-complementarity level is scores given depending on unfavorability of the bonds between nucleotide bases A, T, G and C.

8. The method according to claim 2, wherein the one or more non-hybridizable-non-complementary regions in the target nucleic acid sequence is selected in the step (b) such that they comprise no nucleotides involved in Watson-Crick base pairing with the first tagging part.

9. The method according to claim 2, wherein the one or more non-hybridizable-non-complementary regions in the target nucleic acid sequence are selected in the step (b) such that they are Watson-Crick base paired with 80% or less of nucleotides of the second tagging part based on the total nucleotides number of the second tagging part.

10. The method according to claim 1, wherein the non-hybridizable-non-complementary nucleotide sequence of the tagging portion is selected from sequences that satisfy one or more of the following criteria:
(i) exclusion of a mononucleotide run sequence, $(A)_n$, $(T)_n$, $(G)_n$ or $(C)_n$, in which n is at least 4;
(ii) inclusion of a sequence with 30-80% GC content;
(iii) exclusion of a sequence of the tagging portion immediately adjacent to the targeting portion in which G and/or C is consecutively located in the number of 8 or more;
(iv) when the tagging portion forms a homodimer, exclusion of a sequence in which the ratio of nucleotides involved in the formation of the homodimer is 70% or more based on a total nucleotide number of the tagging portion;
(v) when the tagging portion forms a homodimer, exclusion of a sequence in which the ratio of consecutive nucleotides involved in the formation of the homodimer is 65% or more based on a total nucleotide number of the tagging portion;
(vi) when the tagging portion forms the tagging oligonucleotide together with the targeting portion, exclusion of a sequence rendering ΔG value for a hairpin structure of the tagging oligonucleotide to become −8.0 kcal/mol or less;
(vii) when there is a complementary nucleotide in the first tagging part, exclusion of a sequence in which the complementary nucleotide is located at a position of 0-1 nucleotide apart from a nucleotide of the first tagging part immediately adjacent to the targeting portion;
(viii) inclusion of a sequence in which a nucleotide of the first tagging part immediately adjacent to the targeting portion is A or T;
(ix) when the tagging portion forms a heterodimer with a primer for amplification of the target nucleic acid sequence, exclusion of a sequence in which the ratio of nucleotides involved in the formation of the heterodimer is 40% or more based on a total nucleotide number of the tagging portion; and
(x) when the tagging portion forms a heterodimer with a primer for amplification of the target nucleic acid sequence, exclusion of a sequence in which the ratio of consecutive nucleotides involved in the formation of the heterodimer is 40% or more based on a total nucleotide number of the tagging portion.

11. The method according to claim 2, wherein the predetermined length of the nucleotide sequence in the target nucleic acid sequence in the step (c) is 6-50 nucleotides.

12. The method according to claim 1, wherein the nucleotide sequence of the targeting portion is selected from sequences that satisfy one or more of the following criteria:
(i) inclusion of a sequence with 30-80% GC content;
(ii) inclusion of a sequence having a $T_m$ value of 35° C. to 85° C.;
(iii) when the tagging oligonucleotide is a probe used with a primer for amplifying the target nucleic acid sequence, inclusion of a sequence having a $T_m$ value being 5° C. to 20° C. higher than a $T_m$ value of the primer; and
(iv) when the tagging oligonucleotide is used in a cleavage reaction by 5' nuclease activity, inclusion of a sequence of which 5'-end or 5'-penultimate nucleotide is G or C.

13. The method according to claim 1, wherein the tagging oligonucleotide prepared is selected from oligonucleotides that satisfy one or more of the following criteria:
(i) exclusion of a tagging oligonucleotide in which ΔG value for a hairpin structure is −8.0 kcal/mol or less;
(ii) when the tagging oligonucleotide forms a homodimer, exclusion of a tagging oligonucleotide in which the ratio of nucleotides involved in the formation of the homodimer is 70% or more;
(iii) when the tagging oligonucleotide forms a homodimer, exclusion of a tagging oligonucleotide in which the ratio of consecutive nucleotides involved in the formation of the homodimer is 65% or more;
(iv) when the tagging oligonucleotide forms a heterodimer with another oligonucleotide, exclusion of a tagging oligonucleotide in which the ratio of nucleotides involved in the formation of the heterodimer is 70% or more; and
(v) when the tagging oligonucleotide forms a heterodimer with another oligonucleotide, exclusion of a tagging oligonucleotide in which the ratio of consecutive nucleotides involved in the formation of the heterodimer is 65% or more.

14. The method according to claim 1, wherein the non-hybridizable-non-complementary nucleotide sequence of the tagging portion is selected such that a non-complementarity level of an entire sequence of the tagging portion satisfies a predetermined threshold value criterion.

15. The method according to claim 6, wherein the unfavorability is a weighted unfavorability in which weighting values are assigned to the tagging portion in a successively increasing manner from a location of the second tagging part most distant from the targeting portion to a location of the first tagging part most adjacent to the targeting portion.

16. The method according to claim 1, wherein the hybridizable-complementary nucleotide sequence of the targeting portion is first selected and then as the tagging portion selected is the non-hybridizable-non-complementary nucleotide sequence to a sequence of the target nucleic acid sequence adjacent to a sequence with which the targeting portion is hybridized.

17. A computer readable storage medium containing instructions to configure a processor to perform a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, the method comprising:
(a) selecting the hybridizable-complementary nucleotide sequence to the target nucleic acid sequence for the targeting portion and the non-hybridizable-non-complementary nucleotide sequence to the target nucleic acid sequence for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the target nucleic acid sequence; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and (b) preparing the tagging oligonucleotide comprising (i) the targeting portion comprising the selected hybridizable-complementary nucleotide sequence and (ii) the tagging portion comprising the selected non-hybridizable-non-complementary nucleotide sequence.

18. A computer readable storage medium containing instructions to configure a processor to perform a method for preparing a tagging oligonucleotide comprising a targeting portion comprising a hybridizable-complementary nucleotide sequence to a target nucleic acid sequence and a tagging portion comprising a non-hybridizable-non-complementary nucleotide sequence to the target nucleic acid sequence, the method comprising:

(a) providing a nucleotide sequence for the tagging portion; wherein the tagging portion comprises a first tagging part adjacent to the targeting portion and a second tagging part adjacent to the first tagging part;

(b) selecting in the target nucleic acid sequence one or more non-hybridizable-non-complementary regions to the nucleotide sequence for the tagging portion by (i) selecting at least one region in the target nucleic acid sequence and (ii) evaluating a non-complementarity level of the selected at least one region to the nucleotide sequence for the tagging portion;

(c) selecting a nucleotide sequence for the targeting portion by (i) selecting a nucleotide sequence with a predetermined length in the target nucleic acid sequence that is adjacent to the non-hybridizable-non-complementary region to the nucleotide sequence of the tagging portion and (ii) selecting a hybridizable-complementary nucleotide sequence to the selected nucleotide sequence in the target nucleic acid as the nucleotide sequence for the targeting portion; and (d) preparing the tagging oligonucleotide comprising the nucleotide sequence of the tagging portion provided in the step (a) and the nucleotide sequence of the targeting portion selected in the step (c).

* * * * *